(12) United States Patent
Burk et al.

(10) Patent No.: US 9,090,595 B2
(45) Date of Patent: Jul. 28, 2015

(54) REDUCED CENTRAL CORNEAL THICKENING BY USE OF HYDROPHILIC ESTER PRODRUGS OF BETA-CHLOROCYCLOPENTANES

(71) Applicant: Allergan, Inc., Irvine, CA (US)

(72) Inventors: Robert M. Burk, Laguna Beach, CA (US); Wha Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/185,556

(22) Filed: Feb. 20, 2014

(65) Prior Publication Data

US 2014/0171661 A1 Jun. 19, 2014

Related U.S. Application Data

(63) Continuation-in-part of application No. 13/974,975, filed on Aug. 23, 2013.

(60) Provisional application No. 61/693,437, filed on Aug. 27, 2012.

(51) Int. Cl.
| | |
|---|---|
| *C07D 409/14* | (2006.01) |
| *C07D 333/40* | (2006.01) |
| *C07D 409/12* | (2006.01) |
| *A61K 9/00* | (2006.01) |
| *C07D 333/38* | (2006.01) |

(52) U.S. Cl.
CPC ............ *C07D 409/14* (2013.01); *A61K 9/0048* (2013.01); *C07D 333/38* (2013.01); *C07D 333/40* (2013.01); *C07D 409/12* (2013.01)

(58) Field of Classification Search
CPC .................................................... C07D 409/14

USPC .......................................................... 549/60
See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,353,000 | B1 | 3/2002 | Sallee et al. |
| 2005/0038287 | A1 | 2/2005 | Scherer et al. |
| 2007/0254920 | A1 | 11/2007 | DeLong et al. |
| 2008/0015231 | A1 | 1/2008 | Old et al. |
| 2009/0239869 | A1 | 9/2009 | Donde et al. |
| 2009/0270396 | A1 | 10/2009 | Old et al. |
| 2010/0210689 | A1 | 8/2010 | Old et al. |
| 2011/0124736 | A1 | 5/2011 | Trogden et al. |

FOREIGN PATENT DOCUMENTS

| | | |
|---|---|---|
| WO | 9605309 | 2/1996 |
| WO | 2006047466 | 5/2006 |

OTHER PUBLICATIONS

King, Med. Chem., Principle and Practice (1994), pp. 206-208.*
Patent Cooperation Treaty, The International Search Report and the Written Opinion of the International Searching Authority, PCT Application No. PCT/US2013/056418, Nov. 8, 2013.
Remington's Pharmaceutical Sciences, 17th Edition, 1985, Mack Publishing Company, Easton, PA.
Berg et al., Pharmaceutical Salts, Journal of Pharmaceutical Sciences, 66, 1977, pp. 1-19.

* cited by examiner

*Primary Examiner* — Taofiq A Solola
(74) *Attorney, Agent, or Firm* — Jonathan Y. Bass

(57) ABSTRACT

Compositions and methods for treating glaucoma are provided. In particular hydrophilic ester prodrugs and their use to reduce central corneal thickening is provided.

6 Claims, No Drawings

REDUCED CENTRAL CORNEAL THICKENING BY USE OF HYDROPHILIC ESTER PRODRUGS OF BETA-CHLOROCYCLOPENTANES

CROSS REFERENCE TO RELATED APPLICATIONS

This application is a continuation-in-part of U.S. application Ser. No. 13/974,975, filed Aug. 23, 2013, which claims the benefit of U.S. provisional application Ser. No. 61/693,437, filed on Aug. 27, 2012, all of which applications are incorporated herein by reference in their entireties.

FIELD OF THE INVENTION

The present invention is directed to amino-oxoalkyl ester prodrugs and their use in lowering intraocular pressure and treating glaucoma.

BACKGROUND OF THE INVENTION

Glaucoma is one of the leading causes of blindness in the world, with over 2.5 million people in the United States suffering from the disease and several million more being at risk of developing glaucoma. As the population ages, the number of individuals suffering from glaucoma will continue to grow since the elderly are being affected disproportionally.

Based on its etiology, glaucoma can be classified into primary and secondary glaucoma. Primary glaucoma, also known as congenital glaucoma, can occur in the absence of other ocular conditions and its underlying causes are not known. However, it is known that increased intraocular pressure (IOP) observed in primary glaucoma is due to the obstruction of aqueous humor flow out of the eye. Secondary glaucoma results from another pre-existing ocular disease such as, uveitis, an intraocular tumor, enlarged cataract, central retinal vein occlusion, trauma to the eye, operative procedures and intraocular hemorrhage. Generally, any interference with the outward flow of aqueous humor from the posterior chamber into the anterior chamber and subsequently, into the canal of Schlemm can lead to secondary glaucoma.

Current treatments for glaucoma aim to reduce the pressure in the eye by decreasing the amount of aqueous fluid being produced or alternatively by enhancing the flow of fluid out of the eye by using mechanical means. Agents for topical application used to treat glaucoma include miotics (e.g. Isopto®Carpine, Ocusert®, Pilocar®, and Pilopine®) and epinephrines (e.g. Epifrin® and Propine®), which increase the outflow of fluid; beta blockers (e.g. Betagan®, Betimol®, Betoptic®, Ocupress®, Timoptic®, Optipranalol®), carbonic anhydrase inhibitors and alpha adrenergic agonists (e.g. Alphagan®, Iopidine®, Trusopt®), which reduce the amount of fluid; and prostaglandin analogs (e.g. Lumigan®, Rescula®, Travatan®, Xalatan®), which increase the outflow of fluid through a secondary drainage route.

The topical application of ophthalmic compositions for the treatment of glaucoma requires penetration of the drug through the cornea and into the anterior chamber, which contains aqueous humor, which then drains into the conventional outflow pathway. Intraocular pressure is lowered by drugs acting in the Schlemm's canal and the uveal-scleral pathway. Penetration of the drug through the cornea requires a balance of hydrophobic and hydrophilic characteristics. In order to diffuse into the cornea the drug must be sufficiently soluble in non-polar media and it must be sufficiently soluble in aqueous media in order to diffuse out of the cornea into the aqueous humor.

Potentially useful drugs for the treatment of glaucoma can be delivered as prodrug esters. The use of prodrug esters, which are cleaved enzymatically (e.g. in the cornea) to regenerate the active compound, can enhance penetration of the drug through the cornea into the anterior chamber. However, many esters are too hydrophobic to diffuse out of the relatively non-polar external layer of the cornea and into the aqueous humor. Further, such compounds are often not sufficiently soluble to formulate in aqueous solutions. There is a need in the art for ophthalmic compositions having the capability to penetrate through the cornea into the anterior chamber. At the same time such compositions need to exhibit sufficient hydrophilic properties to formulate in aqueous solution and to be soluble in the anterior chamber. Provided herein are compositions and methods addressing these and other needs in the art.

SUMMARY OF THE INVENTION

In one aspect, a compound having the formula

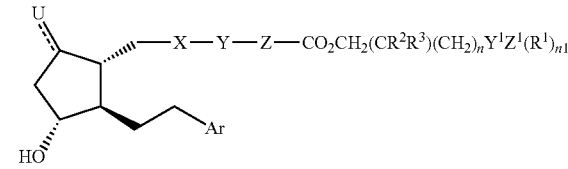

wherein:
X is $CH_2CH_2$, cis-CH=CH, interaylene, $CH_2S$, $CH_2O$ or alkyne,
Y is $C_1$-$C_3$ alkyl, O, S a single bond, a double bond, or thiophene,
Z is interarylene, $C_1$-$C_3$ alkyl, $SCH_2$, $OCH_2$, a single bond or double bond,
U is O, Cl, H—CL, H—H, H—OH, H—Cl, H—F or H—CN and wherein the dashed bond represents a single or double bond,
$R^1$ is independently selected from the group consisting of H, $C_1$-$C_6$ alkyl and $C_1$-$C_6$ hydroxyalkyl, —OH, and

$R^2$ is independently selected from the group consisting of H, $C_1$-$C_6$ alkyl, $C_1$-$C_6$ hydroxyalkyl, and —OH,
$R^3$ is independently H, $C_1$-$C_6$ alkyl and $C_1$-$C_6$ hydroxyalkyl, —OH or R,
n is 0-8,
$Y^1$ is C=O or a single bond,
$Z^1$ is N, NH, NH2, CH2, or —OH
n1 is 0-2,
R is H, alkyl and $CH_2OH$,
Ar is aryl or heteroaryl being mono-, di- or tri-substituted and substituted selected from the group consisting of $C_1$-$C_6$ alkyl, hydroxyalkyl, aryl, halogen, OR, $CF_3$, $C(O)R^4$, $COF_3$, $SO_2N(R4)_2$, $SO_2NH_2$, $NO_2$ and CN wherein the substituted compounds may be the same of different;

$R^4$ is H, $C_1$-$C_6$ alkyl and alkylaryl or independently selected from H, $C_1$-$C_6$ alkyl and alkylaryl.

In another aspect, an ophthalmic pharmaceutical composition including the compound provided herein and embodiments thereof and a pharmaceutically acceptable carrier is provided.

In another aspect, a method of treating an ophthalmic disease in a human is provided. The method includes administering a therapeutically effective amount of the compound provided herein and embodiments thereof to a subject in need thereof.

In another aspect, a method of reducing corneal thickening is provided. The method includes administering a therapeutically effective amount of the compound provided herein and embodiments thereof to a subject in need thereof.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or combination thereof, which may be fully saturated (referred to herein as a "saturated alkyl"), mono- or polyunsaturated and can include di- and multivalent radicals, having the number of carbon atoms designated (i.e. $C_1$-$C_{10}$ means one to ten carbons). In some embodiments, all alkyls set forth as a substituent of the compounds provided herein are saturated alkyls. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. An "alkoxy" is an alkyl attached to the remainder of the molecule via an oxygen linker (—O—). An "alkylthio" is an alkyl attached to the remainder of the molecule via an sulfur linker (—S—). A "haloalkoxy" is an alkoxy substituted with a halogen. When the halogen is a fluoro, it is referred to herein as a "fluoroalkoxy." The term "alkyl" includes saturated alkyl, alkenyl and alkynyl. A saturated alkyl may have from 1 to 10 or 1 to 6 carbon atoms. The term "alkenyl" by itself or as part of another substituent, means, unless otherwise stated, a straight (i.e. unbranched) or branched hydrocarbon chain (e.g., two to ten, or two to six carbon atoms) having one or more double bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the like. The term "alkynyl" by itself or as part of another substituent, means, unless otherwise stated, a straight (i.e. unbranched) or branched hydrocarbon chain (e.g., two to ten or two to six carbon atoms) having one or more triple bonds. Examples of alkynyl groups include, but are not limited to, ethynyl, 1- and 3-propynyl, 3-butynyl, and the like.

The term "alkylene", "alkenylene", and "alkynylene" by itself or as part of another substituent means a divalent radical derived from an alkyl, alkenyl, or alkynyl as exemplified, but not limited, by methylene, ethylene, —$CH_2CH_2CH_2CH_2$—, vinylene and the like.

The term "amino" as used herein means a —$NH_2$. The term "carboxy" as used herein means —COOH.

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si or S, and wherein the nitrogen and sulfur atoms may optionally be oxidized and the nitrogen heteroatom may optionally be quaternized. (Original) The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N(CH_3)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—N(CH_3)—$CH_3$, —O—$CH_3$, —O—$CH_2$—$CH_3$, and —CN. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom.

The terms "cycloalkyl" and "heterocycloalkyl," by themselves or in combination with other terms, represent, unless otherwise stated, non-aromatic cyclic versions of "alkyl" and "heteroalkyl", respectively (e.g., having 4 to 8 ring atoms). Additionally, for heterocycloalkyl, a heteroatom can occupy the position at which the heterocycle is attached to the remainder of the molecule. Heterocycloalkyls may include one or two ring heteroatoms selected from N, O, or $S(O)_{n'}$, where n' is an integer from 0 to 2, the remaining ring atoms being carbon. The heterocycloalkyl or cycloalkyl ring is optionally fused to one or more aryl or heteroaryl rings as defined herein (e.g., where the aryl and heteroaryl rings are monocyclic). The heterocycloalkyl or cycloalkyl ring fused to monocyclic aryl or heteroaryl ring may be referred to in this application as "bicyclic heterocycloalkyl" ring or a "bicyclic cycloalkyl" ring. Additionally, one or two ring carbon atoms in the heterocycloalkyl ring can optionally be replaced by a —CO— group. More specifically the term heterocycloalkyl includes, but is not limited to, pyrrolidino, piperidino, homopiperidino, 2-oxopyrrolidinyl, 2-oxopiperidinyl, morpholino, piperazino, tetrahydropyranyl, thiomorpholino, dihydroindolyl, and the like. When the heterocycloalkyl ring is unsaturated it can contain one or two ring double bonds provided that the ring is not aromatic. When the heterocycloalkyl group contains at least one nitrogen atom, it may also be referred to herein as heterocycloamino and is a subset of the heterocycloalkyl group. When the heterocycloalkyl group is a saturated ring and is not fused to aryl or heteroaryl ring as stated above, it may be referred to herein as a saturated monocyclic heterocycloalkyl. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, an aromatic substituent which can be a single ring or multiple rings (preferably from 1 to 3 rings) which may be fused together (i.e. a fused ring aryl) or linked covalently. A fused ring aryl refers to multiple rings fused together wherein at least one of the fused rings is an aryl ring (e.g., phenyl, 1-naphthyl, 2-naphthyl, or 4-biphenyl). The term "heteroaryl" refers to aryl groups (or rings) that contain one or more (e.g., 4) heteroatoms selected from N, O, and S, wherein the nitrogen and sulfur atoms are optionally oxidized, and the nitrogen atom(s) are optionally quaternized, the remaining ring atoms being carbon. The heteroaryl may be a monovalent monocyclic, bicyclic, or tricyclic (e.g., monocyclic or bicyclic) aromatic radical of 5 to 14 (e.g., 5 to 10) ring atoms where one or more, (e.g., one, two, or three or four) ring atoms are heteroatom selected from N, O, or S. Examples include, but are not limited to, thienyl, isoindolyl, benzoxazolyl, pyridazinyl, triazolyl, tetrazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, 2-benzimidazolyl, 5-indolyl, 1-isoquinolyl, 5-isoquinolyl, 2-quinoxalinyl, 5-quinoxalinyl, 3-quinolyl, and 6-quinolyl. Thus, the term "heteroaryl" includes fused ring heteroaryl groups (i.e. multiple rings fused together wherein at least one of the fused rings is a heteroaromatic ring). A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. An "arylene" and a "heteroarylene," alone or as part of another substituent means a divalent radical derived from an aryl and heteroaryl, respectively.

The terms "arylalkyl" and "heteroarylalkyl" is meant to include those radicals in which an aryl group or a heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom. The term "carbonyl" as used herein refers to a —C(O)— group.

The symbol "~~~" indicates, as customary in the art, the point of attachment of a substituent.

"Optional" or "optionally" means that the subsequently described event or circumstance may but need not occur, and that the description includes instances where the event or circumstance occurs and instances in which it does not. For example, "heterocycloalkyl group optionally substituted with an alkyl group" means that the alkyl may but need not be present, and the description includes situations where the heterocycloalkyl group is substituted with an alkyl group and situations where the heterocycloalkyl group is not substituted with alkyl.

The term "alkylsulfonyl" as used herein means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical unless stated otherwise.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O) NR"R'", —NR"C(O)$_2$R', —NR'—C(NR'R"R'")=NR"", —NR—C(NR'R")=NR"", —S(O)R', —S(O)$_2$R', —S(O)$_2$ NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and may be selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR'R", —NR"C(O)$_2$R', —NR—C(NR'R"R'")=NR"", —NR'—C(NR'R")=NR'", —S(O)R', —S(O)$_2$R', —S(O)$_2$NR'R", —NR'SO$_2$R', —CN and —NO$_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

Unless otherwise stated, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; e.g., the R and S configurations for each asymmetric center as well as cis and trans configurations. Therefore, single stereochemical isomers as well as enantiomeric and diastereomeric mixtures of the present compounds are within the scope of the invention.

The compounds of the present invention may have asymmetric centers and/or geometric isomers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. All possible tautomers and cis and trans isomers, as individual forms and mixtures thereof are within the scope of this invention. Additionally, as used herein the term alkyl includes all the possible isomeric forms of the alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms, including amorphous form, and hydrates of a compound disclosed herein are within the scope of this invention.

Certain compounds of the present invention possess asymmetric carbon atoms (optical centers) or double bonds; the racemates, diastereomers, tautomers, geometric isomers and individual isomers are encompassed within the scope of the present invention, as are enantiomers. The compounds of the present invention do not include those which are known in the art to be too unstable to synthesize and/or isolate.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl.

Unless indicated otherwise, the term "derivative" in the context of a compound disclosed herein refers to a compound afforded by chemical modification, e.g., by the bonding of one or more substituent groups as described herein.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{1A}$-substituted or unsubstituted alkyl, a plurality of $R^{1A}$ substituents may be attached to the alkyl moiety wherein each $R^{1A}$ substituent is optionally different. Where an R-substituted moiety is substituted with a plurality R substituents, each of the R-substituents may be differentiated herein using a prime symbol (') such as R', R", etc. For example, where a moiety is $R^{1A}$-substituted or unsubstituted alkyl, and the moiety is substituted with a plurality of $R^{1A}$ substituents, the plurality of $R^{1A}$ substituents may be differentiated as $R^{1A'}$, $R^{1A''}$, $R^{1A'''}$, etc. In some embodiments, the plurality of R substituents is 3. In some embodiments, the plurality of R substituents is 2.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "prodrug" is used according to its plain ordinary meaning and is intended to mean compounds that require a chemical or enzymatic transformation in order to release the active parent drug in vivo prior to producing a pharmacological effect.

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. (Original) The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and/or causing remission of cancer.

An "effective amount" of a compound is an amount sufficient to contribute to the treatment, prevention, or reduction of a symptom or symptoms of a disease. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. Thus, a prophylactically effective amount may be administered in one or more administrations.

The term "topical" in the context of methods described herein relates in the customary sense to the administration of a compound or pharmaceutical composition which is incorporated into a suitable pharmaceutical carrier and administered at a topical treatment site of a subject. Accordingly, the term "topical pharmaceutical composition" includes those pharmaceutical forms in which the compound is administered externally by direct contact with a topical treatment site, e.g., the eye or the skin. The term "topical ocular pharmaceutical composition" refers to a pharmaceutical composition suitable for administering directly to the eye. The term "topical epidermal pharmaceutical composition" refers to a pharmaceutical composition suitable for administering directed to the epidermal layer of the skin, e.g., the palpebra, the supercilium, the scalp, or the body. The term "topical administering" refers to administering externally by direct contact with a topical treatment site. The term "topical epidermal administering" refers to administering externally by direct contact with the epidermis. The term "topical ocular administering" refers to administering externally by direct contact with the eye.

II. Compositions

Some embodiments of the present invention are illustrated in the following paragraphs:
1) A compound having the formula:

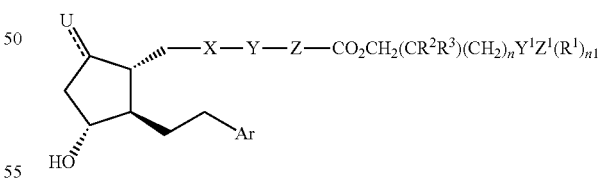

wherein,
X is $CH_2CH_2$, cis-CH=CH, interaylene, $CH_2S$, $CH_2O$ or alkyne,
Y is $C_1$-$C_3$ alkyl, O, S a single bond, a double bond, or thiophene,
Z is interarylene, $C_1$-$C_3$ alkyl, $SCH_2$, $OCH_2$, a single bond or double bond,
U is O, Cl, H—H, H—OH, H—Cl, H—F or H—CN and wherein the dashed bond represents a single or double bond,
$R^1$ is independently selected from the group consisting of H, $C_1$-$C_6$ alkyl and $C_1$-$C_6$ hydroxyalkyl, —OH and

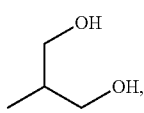

R² is independently selected from the group consisting of H, $C_1$-$C_6$ alkyl, $C_1$-$C_6$ hydroxyalkyl, and —OH,
R³ is independently H, $C_1$-$C_6$ alkyl and $C_1$-$C_6$ hydroxyalkyl, —OH or R,
n is 0-8,
Y¹ is C=O or a single bond,
Z¹ is N, NH, NH2, CH2, or —OH
n1 is 0-2,
R is H, alkyl and $CH_2OH$,
Ar is aryl or heteroaryl being mono-, di- or tri-substituted and substituted selected from the group consisting of $C_1$-$C_6$ alkyl, hydroxyalkyl, aryl, halogen, OR, $CF_3$, $C(O)R^4$, $COF_3$, $SO_2N(R^4)_2$, $SO_2NH_2$, $NO_2$ and CN wherein the substituted compounds may be the same of different;
R⁴ is H, $C_1$-$C_6$ alkyl and alkylaryl or independently selected from H, $C_1$-$C_6$ alkyl and alkylaryl.

2. The compound of paragraph 1 wherein the X is $CH_2CH_2$ or $CH_2CH_2CH_2$.
3. The compound of paragraph 2 wherein Y is thiophene.
4. The compound of paragraph 3 wherein Z is a single bond.
5. The compound of paragraph 4 wherein R² and R³ are H and n is 0 and Y¹ is O.
6. The compound of paragraph 5 wherein Z¹ is N, R¹ is $C_2$ hydroxyalkyl and n¹ is 2.
7. The compound of paragraph 6 wherein Ar is aryl and is disubstituted by Cl and U is Cl.
8. The compound of paragraph 5 wherein Z¹ is N and R¹ is $C_3$ hydroxyalkyl and n1 is 1.
9. The compound of paragraph 8 wherein Ar is aryl and is disubstituted by Cl and U is Cl.
10. The compound of paragraph 4 wherein R² is $C_1$ hydroxyalkyl and R³ is $C_1$ hydroxyalkyl.
11. The compound of paragraph 10 wherein Y¹ is O, Z¹ is N, R¹ is H and n1 is 2.
12. The compound of paragraph 11 wherein Ar is aryl and is disubstituted by Cl and U is Cl.
13. The compound of paragraph 4 wherein R² is $C_1$ hydroxy alkyl and R³ is R.
14. The compound of paragraph 13 wherein R is selected from the group consisting of H, alkyl and $CH_2OH$.
15. The compound of paragraph 14 wherein n is 0, Y¹ is a single bond and Z¹ is $CH_2$.
16. The compound of paragraph 15 wherein R¹ is —OH and n1 is 1.
17. The compound of paragraph 15 wherein Ar is aryl and is disubstituted by Cl and U is Cl.
18. The compound of paragraph 1 selected from the group consisting of:

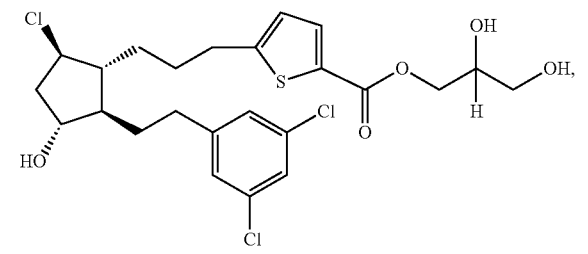

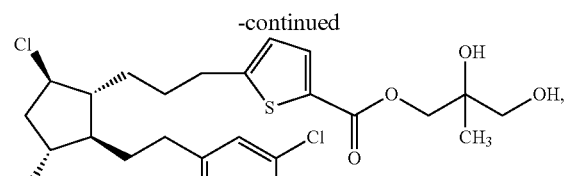

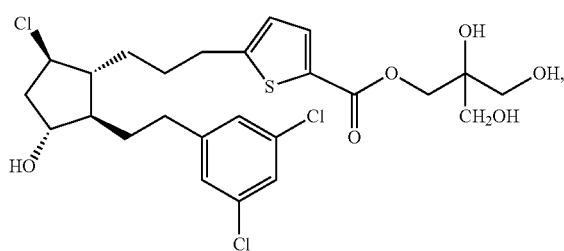

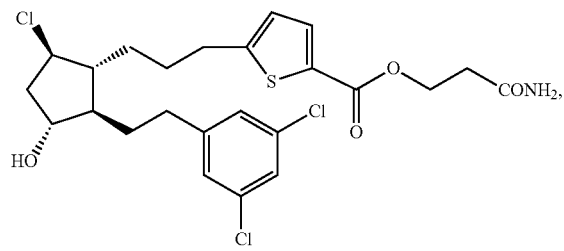

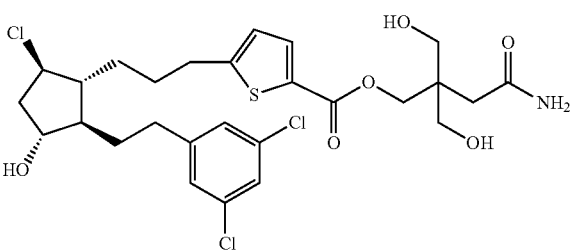

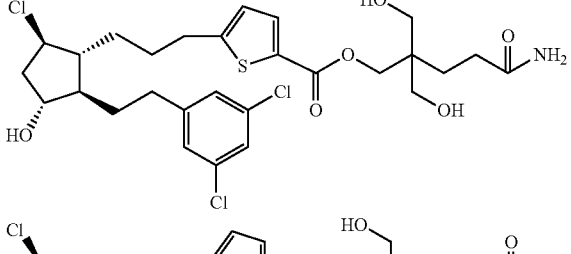

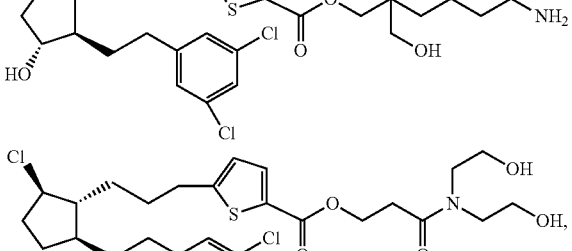

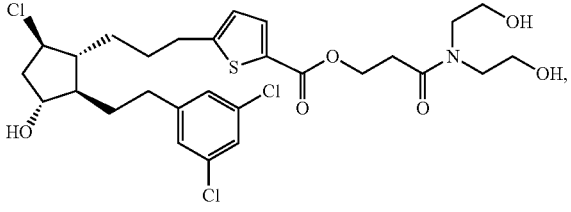

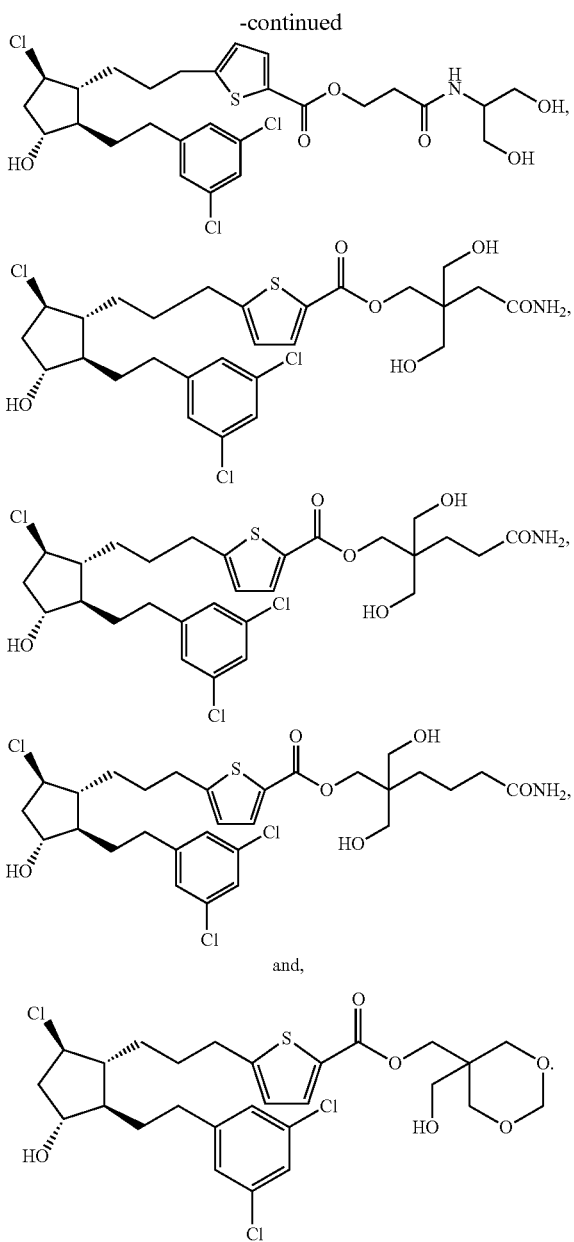

and,

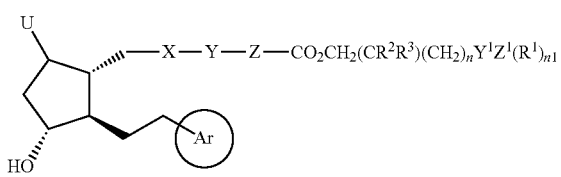

20. The compound of paragraph 1 having the formula:

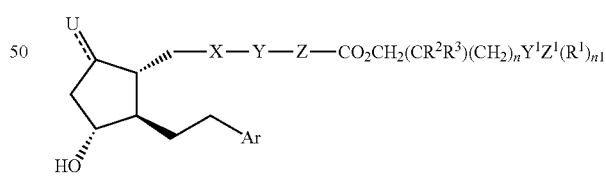

wherein,
X is CH$_2$CH$_2$ or cis-CH=CH,
Y is a single bond, a double bond, or thiophene,
Z is C$_1$-C$_3$ alkyl, SCH$_2$, OCH$_2$, a single bond or double bond,
U is halogen or Cl,
R$^1$ is independent selected from the group consisting of H, —OH, and C1-C3 hydroxy alkyl, R$^2$ is independently selected from the group consisting of H, C$_1$-C$_6$ alkyl, C$_1$-C$_6$ hydroxyalkyl, and —OH,
R$^3$ is independently selected from the group consisting of H, C$_1$-C$_6$ alkyl and C$_1$-C$_6$ hydroxyalkyl, —OH or R,
n is 0-3,
Y$^1$ is C=O or a single bond,
Z$^1$ is N, NH2, CH2, or —OH
n1 is 0-2,
R is H, alkyl and CH$_2$OH, and,
Ar is aryl or heteroaryl being mono-, di- or tri-substituted and substituted selected from the group consisting of halogen and Cl.

21. The compound of paragraph 20 wherein X is CH$_2$CH$_2$.
22. The compound of paragraph 21 wherein Y is thiophene.
23. The compound of paragraph 22 wherein Z is a single bond.
24. The compound of paragraph 22 wherein R$^2$ is —OH, R$^3$ is H, n is 1, Y$^1$ is a single bond, Z$^1$ is —OH and n1 is 0.
25. The compound of paragraph 22 wherein R$^2$ is —OH, R$^3$ is CH$_3$, n is 1, Y$^1$ is a single bond, Z$^1$ is —OH and n1 is 0.
26. The compound of paragraph 22 wherein R$^2$ is —OH, R$^3$ is CH$_2$OH, n is 1, Y$^1$ is a single bond, Z$^1$ is —OH and n1 is 0.
27. The compound of paragraph 22 wherein R$^2$ is C1 hydroxyalkyl, R$^3$ is C1 hydroxyalkyl, n is 1, Y$^1$ is a single bond, Z$^1$ is NH$_2$ and n1 is 0.
28. The compound of paragraph 22 wherein R$^2$ is C1 hydroxyalkyl, R$^3$ is C1 hydroxyalkyl, n is 2, Y$^1$ is a single bond, Z$^1$ is NH$_2$ and n1 is 0.
29. The compound of paragraph 22 wherein R$^2$ is C1 hydroxyalkyl, R$^3$ is C1 hydroxyalkyl, n is 3, Y$^1$ is a single bond, Z$^1$ is NH$_2$ and n1 is 0.
30. The compound of paragraph 22 wherein R2 is H, R3 is H, n is 0, Y1 is C=O and Z1 is N and R1 is C2 hydroxyalkyl and n1 is 2.
31. The compound of paragraph 22 wherein R2 is H, R3 is H, n is 0, Y1 is C=O and Z1 is N and R1 is C2 hydroxyalkyl and n1 is 2.
32. The compounds of paragraphs 22-31 wherein U is Cl and Ar is aryl.
33. The compound of paragraph 32 where aryl is substituted with Cl.
34. The compound of paragraph 33 wherein aryl is di-substituted with Cl.
35) A compound having the formula:

wherein,
X is, C$_1$-C$_3$ alkyl, cis-CH=CH, interarylene, CH$_2$S, CH$_2$O or alkyne,
Y is C$_1$-C$_3$ alkyl, O, S a single bond, a double bond, or thiophene,
Z is interarylene, C$_1$-C$_3$ alkyl, SCH$_2$, OCH$_2$, a single bond or double bond,
U is O, H—H, H—OH, H—Cl, H—F or H—CN and wherein the dashed bond represents a single or double bond,
R$^1$ is independently selected from the group consisting of H, C$_1$-C$_6$ alkyl, C$_1$-C$_6$ hydroxyalkyl, —OH, and

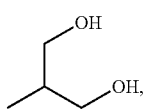

R² is independently selected from the group consisting of H, $C_1$-$C_6$ alkyl, $C_1$-$C_6$ hydroxyalkyl, and —OH,
R³ is independently H, $C_1$-$C_6$ alkyl, $C_1$-$C_6$ hydroxyalkyl, or —OH,
n is 0-3,
Y¹ is C=O, $C_1$-$C_3$ hydroxyalkyl or a single bond,
Z¹ is N, NH, NH2, CH2,

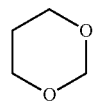

or —OH,
n1 is 0-2,
Ar is aryl or heteroaryl being mono-, di- or tri-substituted and substituted selected from the group consisting of $C_1$-$C_6$ alkyl, hydroxyalkyl, aryl, halogen, OR, $CF_3$, C(O)R⁴, $COF_3$, $SO_2N(R4)_2$, $SO_2NH_2$, $NO_2$ and CN wherein the substituted compounds may be the same or different;
R4 is H, C1-C6 alkyl and alkylaryl or independently selected from H, C1-C6 alkyl and alkylaryl.
36. The compound of paragraph 35 wherein the X is $CH_2CH_2$.
37. The compound of paragraph 36 wherein Y is thiophene.
38. The compound of paragraph 37 wherein Z is a single bond.
39. The compound of paragraph 38 wherein R² is —OH and R³ is H or $CH_3$ and n is 0 and Y¹ is a single bond, Z¹ is —OH and n1 is 0.
40. The compound of paragraph 39 wherein U is H—Cl.
41. The compound of paragraph 40 wherein Ar is aryl and is disubstituted by 4 Cl.
The compound of paragraph 41 wherein R² and R³ are H, n is 0, Y¹ is C=O, Z¹ is N, R¹ is $CH_2CH_2OH$, and n1 is 2.
43. The compound of paragraph 42 wherein Ar is aryl and is disubstituted by Cl and U is H—Cl.
44. The compound of paragraph 43 wherein R² and R³ are H, n is 0, Y¹ is C=O, Z¹ is NH, and R1 is

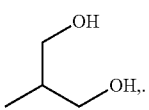

45. The compound of paragraph 44 wherein Ar is aryl and is disubstituted by Cl and U is H—Cl.
46. The compound of paragraph 45 wherein R² and R³ are $CH_2$—OH, n is 1, Y¹ is C=O, Z¹ is $NH_2$, n1 is 0 and Ar is aryl and is disubstituted by Cl and U is Cl.
47. The compound of paragraph 46 wherein R² and R³ are $CH_2$—OH, n is 2, Y¹ is C=O, Z¹ is $NH_2$, n1 is 0 and Ar is aryl and is disubstituted by Cl and U is Cl.
48. The compound of paragraph 47 wherein R² and R³ are $CH_2$—OH, n is 3, Y¹ is C=O, Z¹ is $NH_2$, n1 is 0 and Ar is aryl and is disubstituted by Cl and U is Cl.

49. The compound of paragraph 48 selected from the group consisting of:

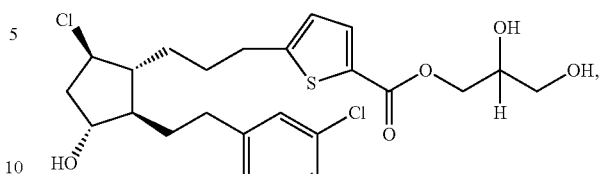

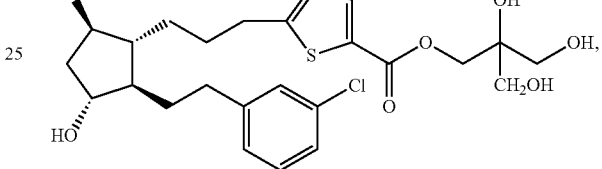

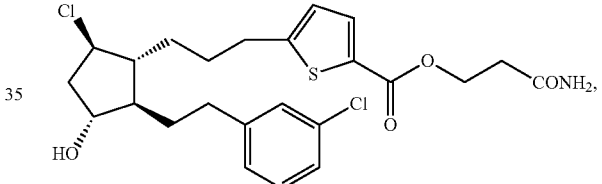

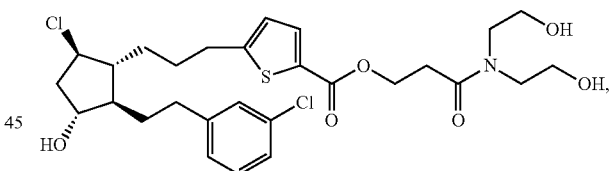

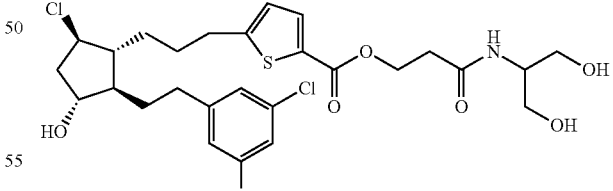

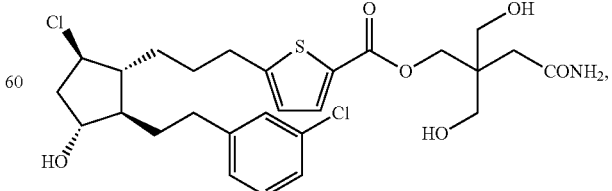

-continued

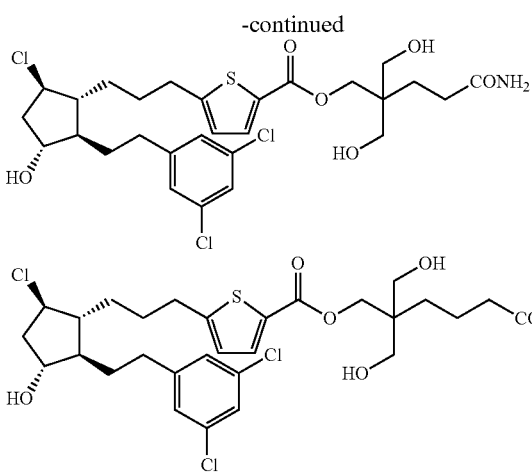

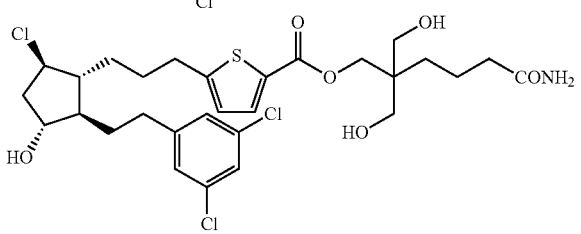

and,

50. The compound of paragraphs 1 or 35 having the formula:

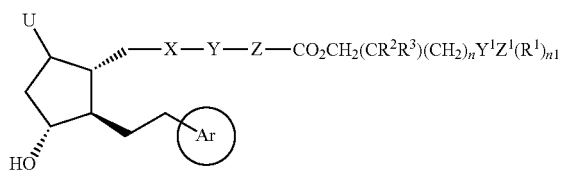

wherein,
X is $C_1$-$C_3$ alkyl and, $CH_2CH_2CH_2$,
Y is a single bond, a double bond, or thiophene,
Z is $C_1$-$C_3$ alkyl, or a single bond,
U is halogen or H—Cl,
$R^1$ is independently selected from the group consisting of H, —OH, and C1-C3 hydroxy alkyl, $CH_2OH$ and

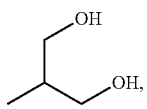

$R^2$ is independently selected from the group consisting of H, $C_1$-$C_6$ alkyl, $C_1$-$C_3$ hydroxyalkyl, or —OH,
$R^3$ is independently selected from the group consisting of H, $C_1$-$C_6$ alkyl and $C_1$-$C_6$ hydroxyalkyl, —OH or R,
n is 0-3,
$Y^1$ is C=O, C1-C3 hydroxyalkyl, $CH_2OH$ or a single bond,
$Z^1$ is N, NH, NH2, —OH
n1 is 0-2,
R is H, alkyl and $CH_2OH$, or,

Ar is aryl or heteroaryl being mono-, di- or tri-substituted and substituted selected from the group consisting of halogen and Cl.
51. A compound according to paragraph 50 wherein X is $CH_2CH_2CH_2$, Y is thiophene, and Z is a single bond.
52. The compound of paragraph 51 wherein $R^2$ is —OH and $R^3$ is H or $CH_3$ and n is 0 and $Y^1$ is a single bond, $Z^1$ is —OH and n1 is 0.
53. The compound of paragraph 52 wherein $R^2$ and $R^3$ are $CH_2$—OH, n is 1-3, $Y^1$ is C=O, $Z^1$ is $NH_2$, n1 is 0 and Ar is aryl and is disubstituted by Cl and U is Cl.
54. A compound selected from the group consisting of:

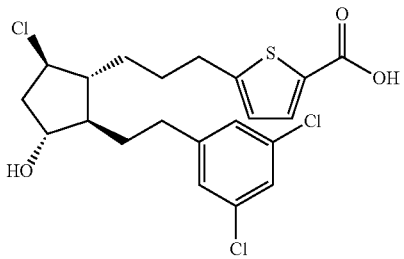

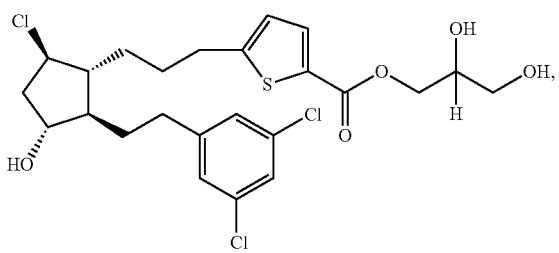

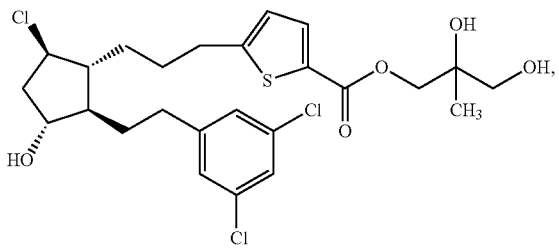

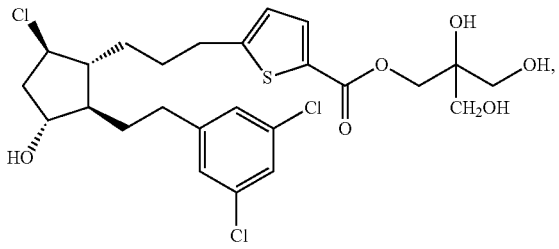

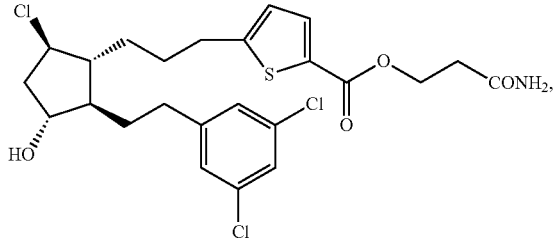

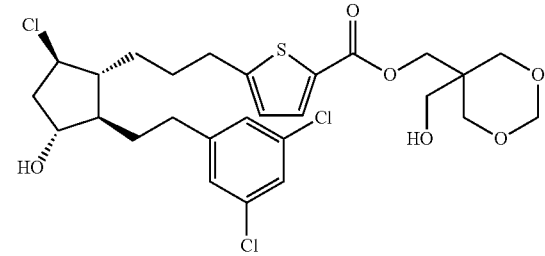

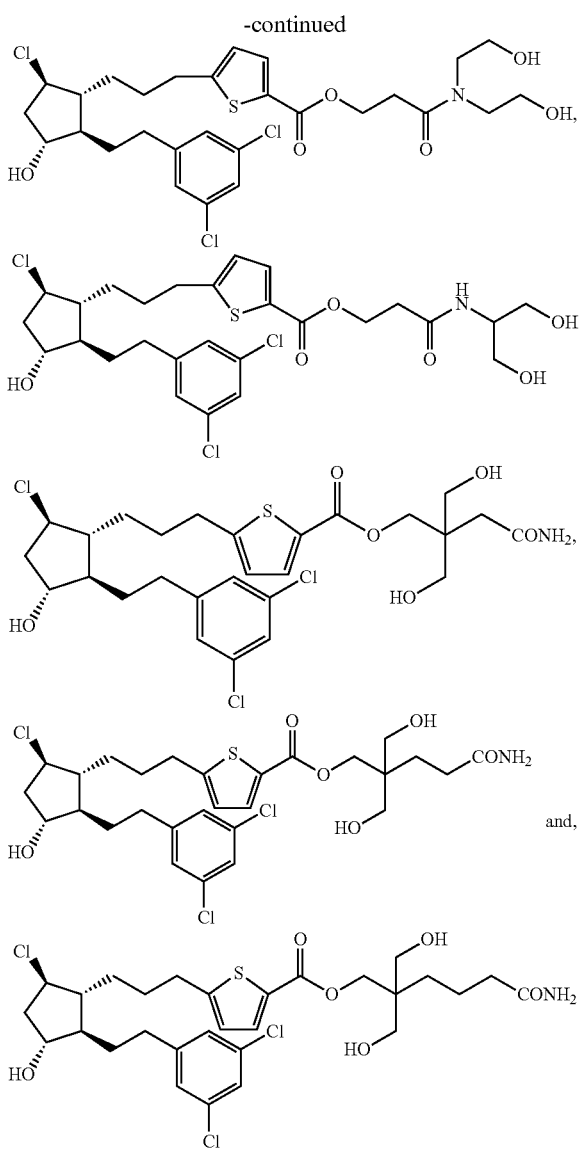

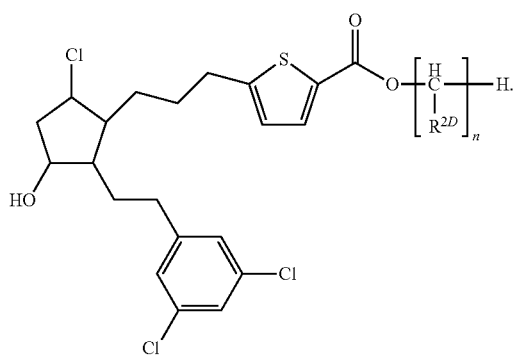

Where the compound has the structure of formula (III), n is 1 to 10, and $R^{2D}$ at each occurrence is independently hydrogen or hydroxyl. In formula (III) n may be 1, 2, 3, 4, 5, 6, 7, 8, 9 or 10. In one embodiment, 1, 2, 3, 4, 5 or 6 $R^{2D}$ substituents are not hydrogen. In one embodiment, 2 $R^{2D}$ substituents are not hydrogen. In one embodiment, 3 $R^{2D}$ substituents are not hydrogen. In one embodiment, 4 $R^{2D}$ substituents are not hydrogen. In one embodiment, 5 $R^{2D}$ substituents are not hydrogen. In one embodiment, 6 $R^{2D}$ substituents are not hydrogen. In one embodiment, 1 $R^{2D}$ substituent is hydroxyl. In one embodiment, 2 $R^{2D}$ substituents are hydroxyl. In one embodiment, 3 $R^{2D}$ substituents are hydroxyl. In one embodiment, 4 $R^{2D}$ substituents are hydroxyl. In one embodiment, n is greater than 1, e.g., 2, 3, 4, 5, 6, 7, 8, 9 or 10. In one embodiment, n is 3 and 2 $R^{2D}$ substituents are hydroxyl. In one embodiment, n is 4 and 3 $R^{2D}$ substituents are hydroxyl. In one embodiment, n is 5 and 4 $R^{2D}$ substituents are hydroxyl. In one embodiment, $R^2$ is not hydroxyethyl.

In one embodiment, the compound has the structure of formula:

(IV)

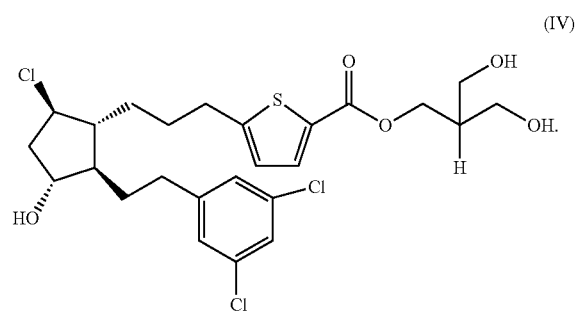 [SMILES: O=C(OCC(CO)CO)c1ccc(CCC[C@@H]2[C@@H](CCc3cc(Cl)cc(Cl)c3)[C@H](O)C[C@H]2Cl)s1]

In one embodiment, the compound has the structure of formula:

(IVa)

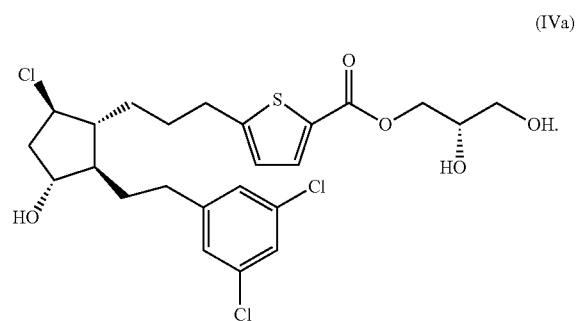 [SMILES: O=C(OC[C@@H](O)CO)c1ccc(CCC[C@@H]2[C@@H](CCc3cc(Cl)cc(Cl)c3)[C@H](O)C[C@H]2Cl)s1]

In one embodiment, the compound has the structure of formula:

(IVb)

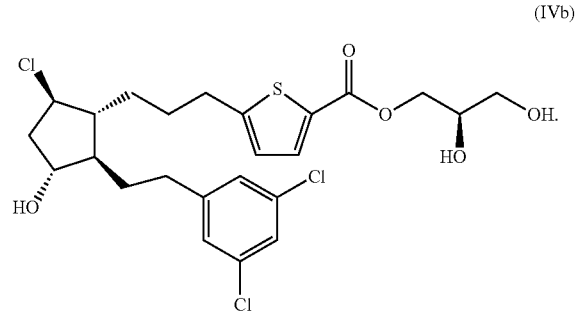 [SMILES: O=C(OC[C@H](O)CO)c1ccc(CCC[C@@H]2[C@@H](CCc3cc(Cl)cc(Cl)c3)[C@H](O)C[C@H]2Cl)s1]

In one embodiment, the compound has the structure of formula:
(V)
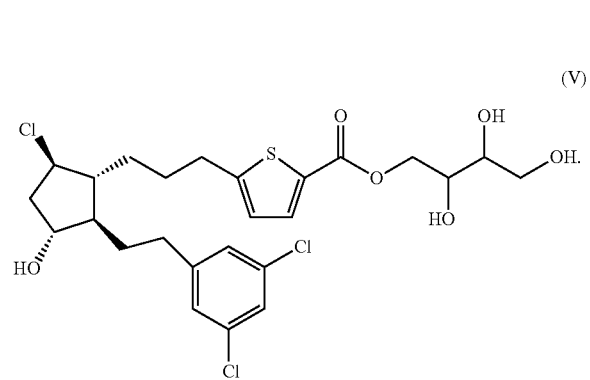 [SMILES: O=C(OCC(O)C(O)CO)c1ccc(CCC[C@@H]2[C@@H](CCc3cc(Cl)cc(Cl)c3)[C@H](O)C[C@H]2Cl)s1]
In one embodiment, the compound has the structure of formula:
(Va)
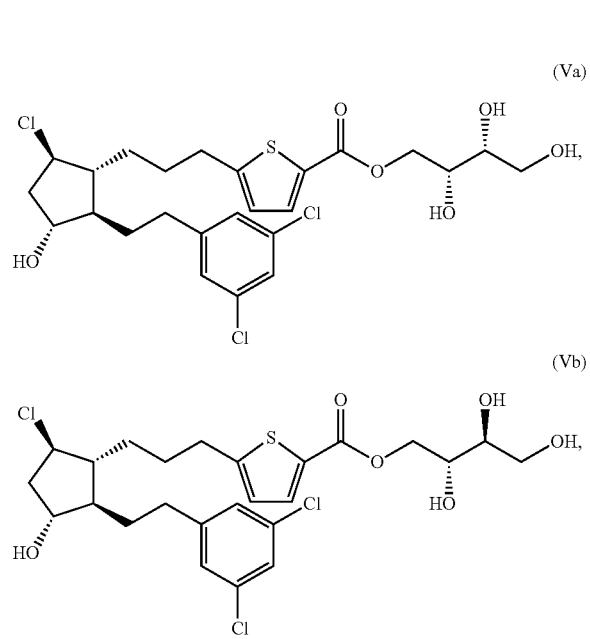
(Vb)
(Vc)
(Vd)
In one embodiment, the compound has the structure of formula:
(VI)
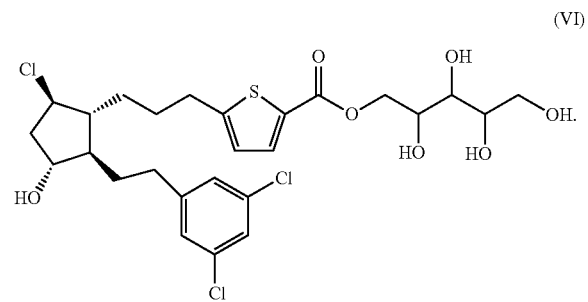 [SMILES: O=C(OCC(O)C(O)C(O)CO)c1ccc(CCC[C@@H]2[C@@H](CCc3cc(Cl)cc(Cl)c3)[C@H](O)C[C@H]2Cl)s1]
In one embodiment, the compound has the structure of formula:
(VIa)
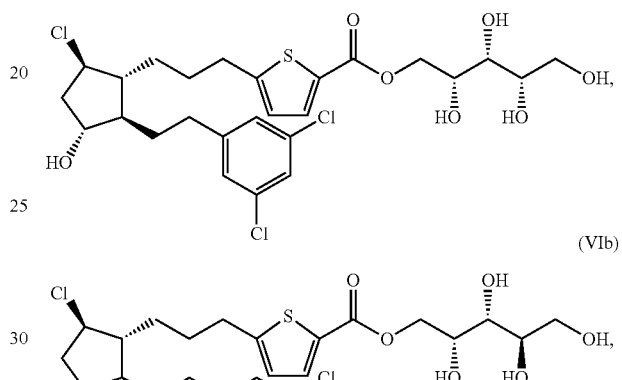
(VIb)
(VIc)
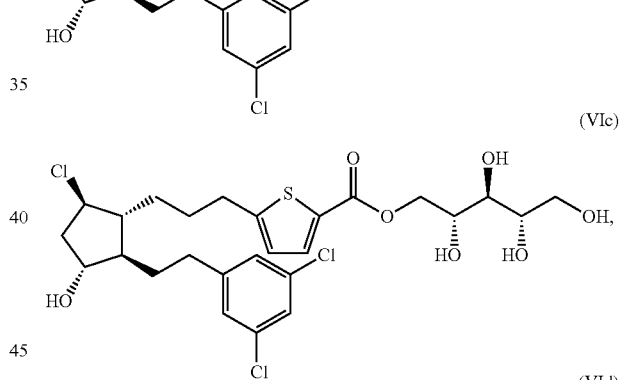
(VId)
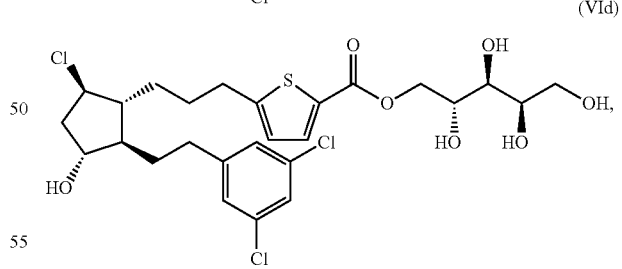
(VIe)
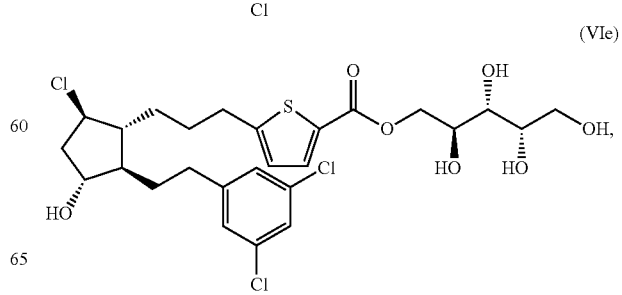

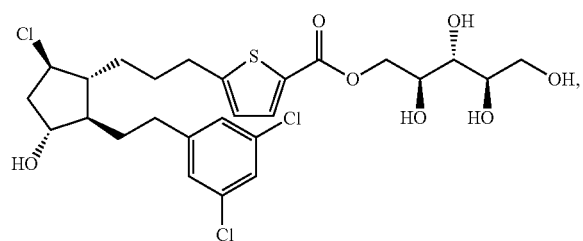
(VIf)
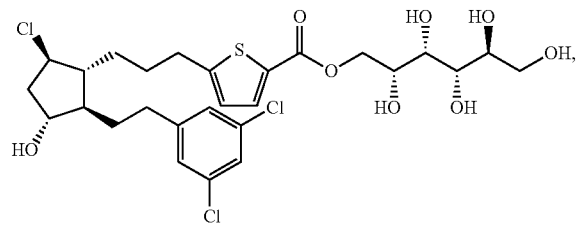
(VIIb)
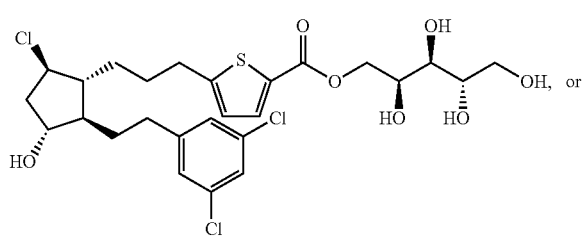
(VIg)
(VIIc)
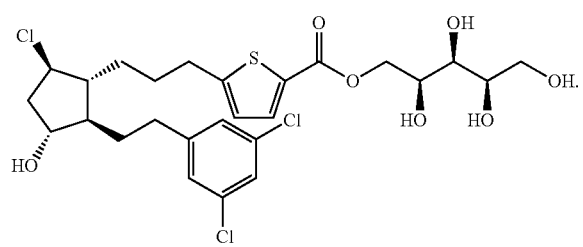
(VIh)
(VIId)
In one embodiment, the compound has the structure of formula:
(VIIe)
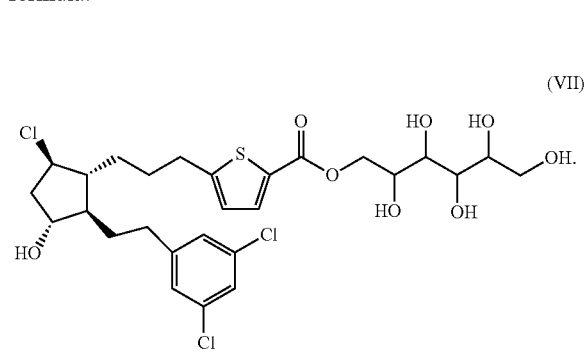
(VII)
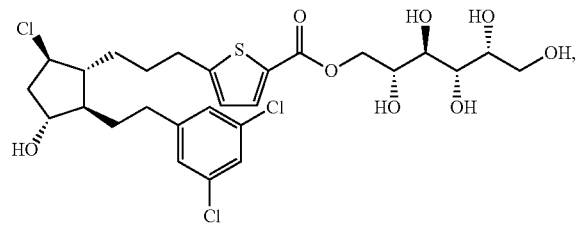
(VIIf)
In one embodiment, the compound has the structure of formula:
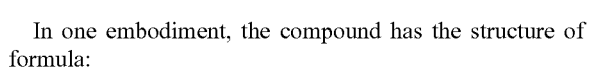
(VIIa)
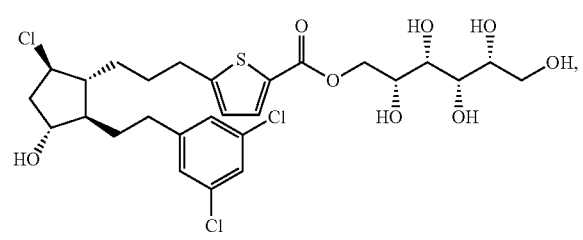
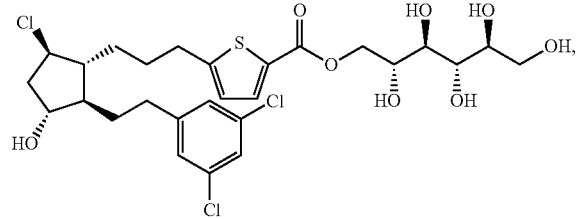
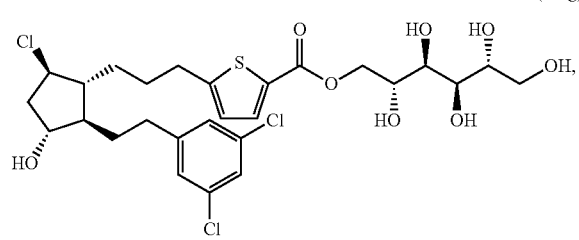
(VIIg)

-continued
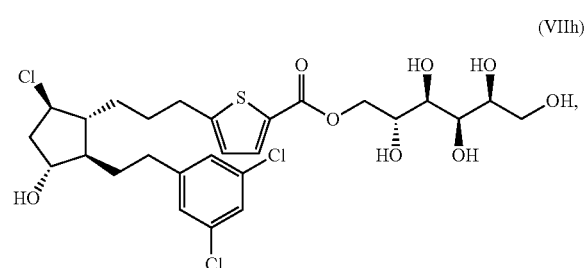
(VIIh)
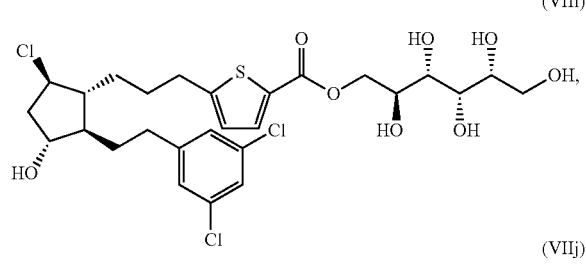
(VIIi)
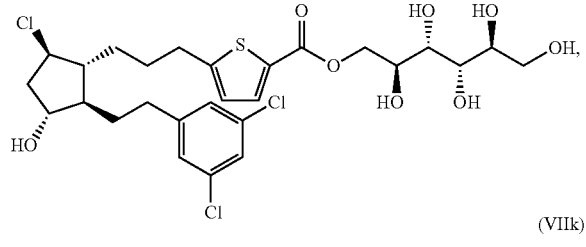
(VIIj)
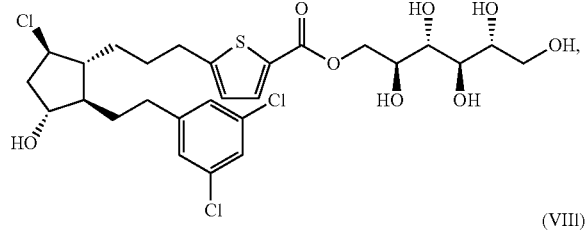
(VIIk)
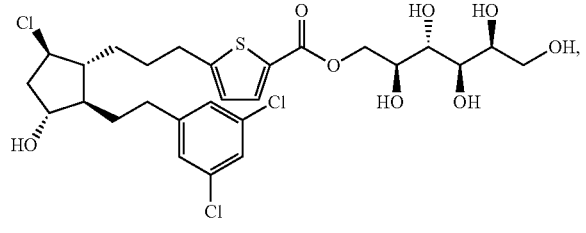
(VIIl)
-continued
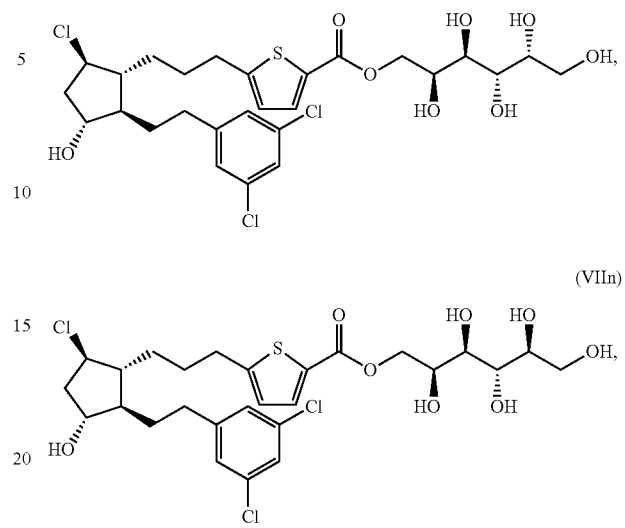
(VIIm)
(VIIn)
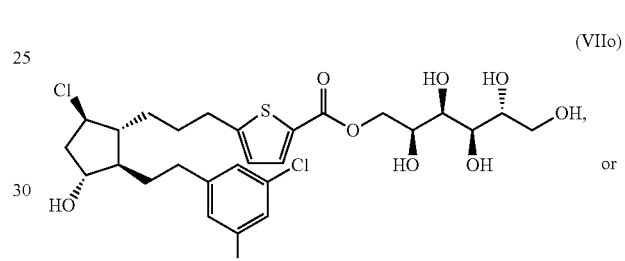
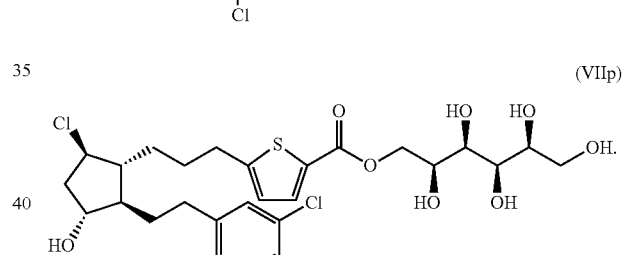
(VIIo)
or
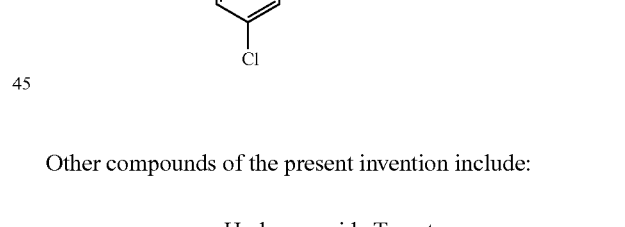
(VIIp)
Other compounds of the present invention include:
Hydroxyamide Targets
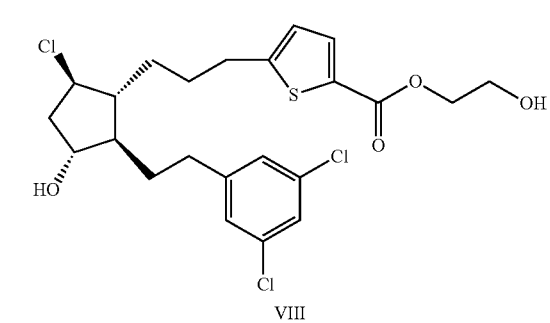
VIII
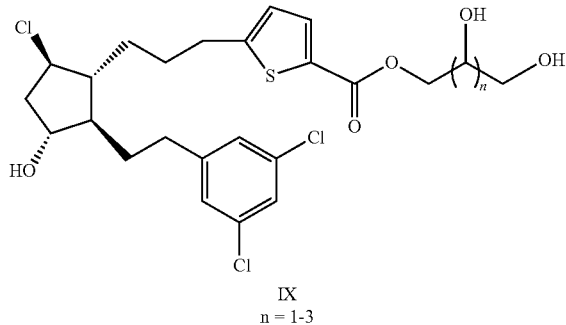
IX
n = 1-3

-continued
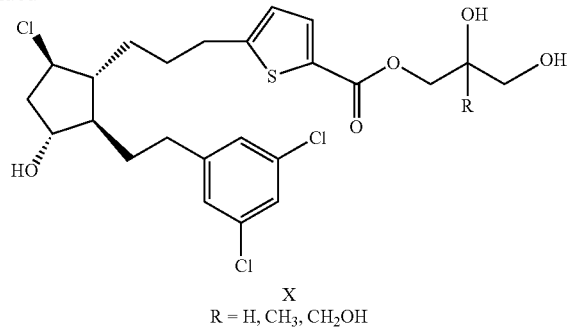
X
R = H, CH₃, CH₂OH
Some embodiments include:
-continued
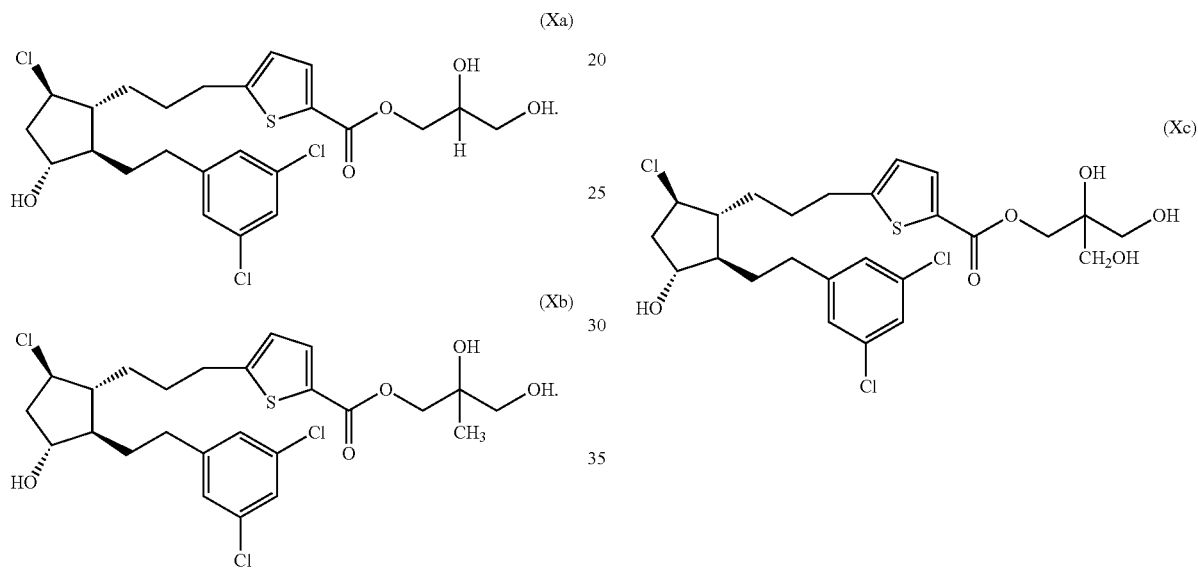
Other compounds of the present invention include:
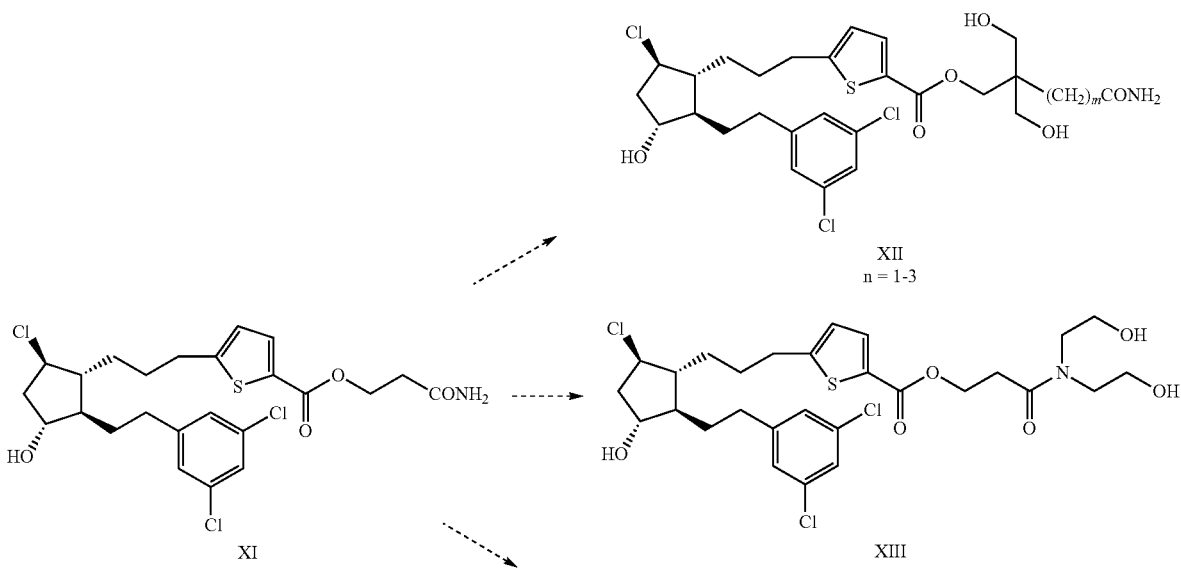

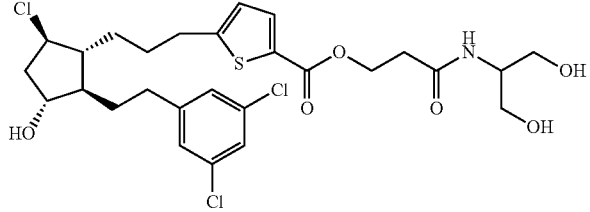

XIV

In one embodiment the compound has the structure:

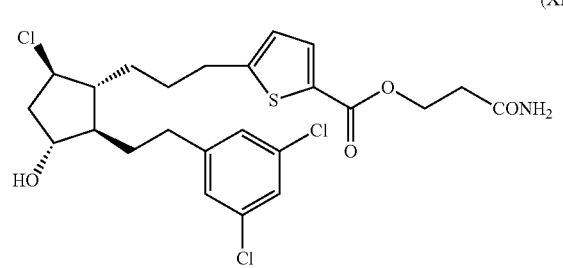

(XI)

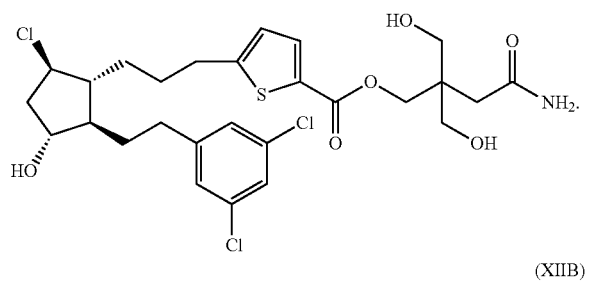

(XIIA)

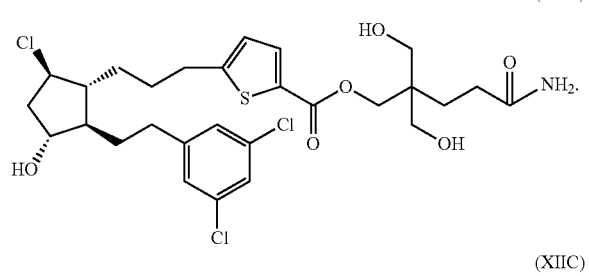

(XIIB)

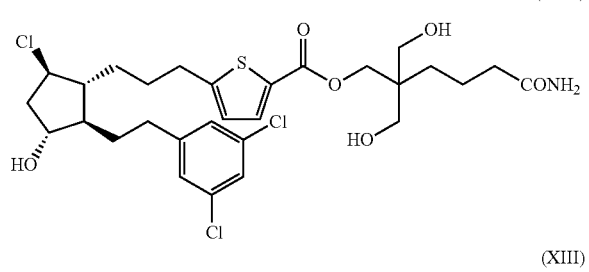

(XIIC)

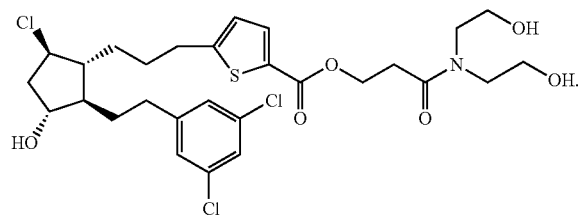

(XIII)

-continued (XIV)

The compounds described herein including embodiments thereof (e.g., a compound with structure of any one of formulae I-XIV or derivative, isomer or enantiomer thereof can be provided.

III. Pharmaceutical Compositions

In another aspect, an ophthalmic pharmaceutical composition including a compound provided herein and embodiments thereof (e.g., a compound of formula I-XIV, or derivative, isomer or enantiomer thereof) is provided. In one embodiment, the compound has the structure of formula (I). In one embodiment, the compound has the structure of formula (III). In one embodiment, the compound has the structure of formula (IV). In one embodiment, the compound has the structure of one of formulae (IVa)-(IVb). In one embodiment, the compound has the structure of formula (V). In one embodiment, the compound has the structure of one of formulae (Va)-(Vd). In one embodiment, the compound has the structure of formula (X). In one embodiment, the compound has the structure of one of formulae (Xa)-(Xc). In one embodiment, the compound has the structure of formula (XI). In one embodiment, the compound has the structure of one of formulae (VIIa)-(VIIp), VIII, IX, X, XI, XII, XIII XIV.

In one embodiment, the pharmaceutical composition is a solution, emulsion, gel or foam. In one embodiment, the pharmaceutical composition is a solution. In one embodiment, the pharmaceutical composition is an emulsion. In one embodiment, the pharmaceutical composition is a gel. In one embodiment, the pharmaceutical composition is a foam.

A. Formulations:

The compounds and pharmaceutical compositions disclosed herein can be prepared and administered in a variety of forms including solution, emulsion, gel or foam. Accordingly, pharmaceutical compositions contemplated herein include a pharmaceutically acceptable carrier or excipient and one or more compounds described herein. "Solution" refers in the customary sense to a liquid pharmaceutical composition in which a compound (e.g., a compound described herein), is at least partially dissolved, preferably fully dissolved, and which can be administered as a liquid. "Emulsion" refers in the customary sense to a mixture of two or more immiscible liquids, one compound (e.g., a compound described herein or solution thereof) being dispersed through the other compound (e.g., a carrier as described herein). "Gel" refers in the customary sense to a highly viscous solution, emulsion, or colloidal suspension of a compound within a continuous fluid phase resulting in a viscous semirigid fluid. "Colloid" refers in the customary sense to a composition which includes a continuous medium throughout which are distributed small particles which do not settle under the influence of gravity. "Foam" refers in the customary sense to a composition which includes a continuous medium (i.e., solution, emulsion, gel and the like) through which gas (e.g., air) is dispersed.

Pharmaceutical compositions contemplated herein may be prepared by combining a therapeutically effective amount of at least one compound as described herein as an active ingredient in combination with one or more conventional pharmaceutically acceptable excipients, and by preparation of unit dosage forms suitable for topical use. The therapeutically efficient amount typically is between about 0.0001 and about 5% (w/v), preferably about 0.001 to about 1.0% (w/v) in liquid formulations which include solutions, emulsions, gels and foams. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760 which are incorporated herein in their entireties. The entire contents of these patents are incorporated herein by reference in their entirety for all purposes. US Patent application publication No. US 2011-0124736 A1, also corresponding to U.S. patent application Ser. No. 12/940,711, is hereby incorporated by reference in its entirety.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity agents may be added as needed or convenient. They include, but are not limited to, salts, particularly sodium chloride, potassium chloride, mannitol and glycerin, or any other suitable ophthalmically acceptable tonicity adjustor.

An ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ophthalmic formulations of the present invention are conveniently packaged in forms suitable for metered application, such as in containers equipped with an orifice, to facilitate application to the eye. Vials suitable for unit dose application are usually made of suitable inert, non-toxic plastic material, and generally contain between about 0.5 and about 15 ml solution, emulsion, gel or foam. One package may contain one or more unit doses.

Preservative-free solutions are often formulated in non-resealable containers containing up to about ten, preferably up to about five units doses, where a typical unit dose is from one to about 8 drops, preferably one to about 3 drops.

Typically, the compounds are applied repeatedly for a sustained period of time topically on the part of the body to be treated, for example, the eye. The preferred dosage regimen will generally involve regular administration for a period of treatment of at least one month, more preferably at least three months, and most preferably at least six months. The regular administration can be 1, 2, 3, 4 or even more times per day.

IV. Methods of Treatment

In another aspect, a method of treating an ophthalmic disease in a human is provided. The method includes administering a therapeutically effective amount of a compound provided herein and embodiments thereof (e.g., a compound of formula I-XIV or derivative, isomer or enantiomer thereof) to a subject in need thereof. In one embodiment, the administering is topical administering. In one embodiment, the disease is macular degeneration. In one embodiment, the disease results from intraocular pressure. In one embodiment, the disease is glaucoma.

In one embodiment, a combination treatment with a -blocker (or -adrenergic antagonist) including carteolol, levobunolol, metipranolol, timolol hemihydrate, timolol maleate, 1-selective antagonists such as betaxolol, and the like.

In one embodiment, a combination treatment with an adrenergic agonists including non-selective adrenergic agonists such as epinephrine borate, epinephrine hydrochloride, and dipivefrin, and the like, or an 2-selective adrenergic agonists such as apraclonidine, brimonidine, and the like.

In one embodiment, a combination treatment with a carbonic anhydrase inhibitors including acetazolamide, dichlorphenamide, methazolamide, brinzolamide, dorzolamide, and the like, is provided.

In one embodiment, a combination treatment with a cholinergic agonist including direct acting cholinergic agonists such as carbachol, pilocarpine hydrochloride, pilocarpine nitrate, pilocarpine, and the like, is provided.

In one embodiment, a combination treatment with a cholinesterase inhibitors such as demecarium, echothiophate, physostigmine, and the like, is provided.

In one embodiment, a combination treatment with a glutamate antagonists or other neuroprotective agents such as $Ca^{2+}$ channel blockers such as memantine, amantadine, rimantadine, nitroglycerin, dextrorphan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-1 01,606, tibalosine, 2309BT, and 840S, flunarizine, nicardipine, nifedipine, nimodipine, barnidipine, verapamil, lidoflazine, prenylamine lactate, amiloride, and the like, is provided.

In one embodiment, a combination treatment with prostamides such as bimatoprost, is provided.

In one embodiment, a combination treatment with a prostaglandin including travoprost, UF0-21, chloroprostenol, fluprostenol, 13,14-dihydro-chloroprostenol, isopropyl unoprostone, latanoprost and the like is provided.

In one embodiment, a combination treatment with a cannabinoid including CB1 agonists such as WIN-55212-2 and CP-55940 and the like, is provided.

In another aspect, a method of reducing corneal thickening is provided. The method includes administering a therapeutically effective amount of a compound provided herein and embodiments thereof (e.g., a compound of formula I-XIV, or derivative, isomer or enantiomer thereof) to a subject in need thereof. In one embodiment, the subject suffers from glaucoma. In one embodiment, the subject suffers from ocular hypertension.

In one embodiment, a method of using a compound disclosed herein for the manufacture of a medicament for the treatment of glaucoma or ocular hypertension is provided. In one embodiment, the compound has the structure of any one of formulae I-XIV. In one embodiment, the compound has the structure of formula (I). In one embodiment, the compound has the structure of formula (Xa-Xc). In one embodiment, the compound has the structure of formula (XI). In one embodiment, the compound has the structure of one of formulae (XIIa)-(XIIc). In one embodiment, the compound has the structure of formula (XIII). In one embodiment, the compound has the structure of one of formulae (XIV). In one embodiment, the compound has the structure of formula (VI). In one embodiment, the compound has the structure of one of formulae (VIa)-(VIh). In one embodiment, the compound has the structure of formula (VII). In one embodiment, the compound has the structure of one of formulae (VIIa)-(VIIp).

V. Examples

Abbreviations used herein have the customary meaning in the chemical arts. Specific abbreviations include the following: TBDMSO: (tert-butyldimethylsilyl)oxy; DMF: dimethylformamide; EDC: 1-ethyl-3-[3-dimethylaminopropyl]carbodiimide hydrochloride; DMAP: 4-dimethylaminopyridine; THF: tetrahydrofuran; $Bu_4NF$: tetrabutylammonium fluoride.

Example 1

Synthesis of (R)-2,3-dihydroxypropyl 5-(3-((1R,2R, 3R,5R)-5-chloro-2-(3,5-dichlorophenethyl)-3-hydroxycyclopentyl)propyl)thiophene-2-carboxylate (compound 3)

An exemplary synthesis of compound 3 is provided in scheme 1 following.

(R)-2,2-dimethyl-1,3-dioxolan-4-yl)methyl 5-(3-((1R,2R,3R,5R)-5-chloro-2-(3,5-dichlorophenethyl)-3-hydroxycyclopentyl)propyl)thiophene-2-carboxylate (compound 2

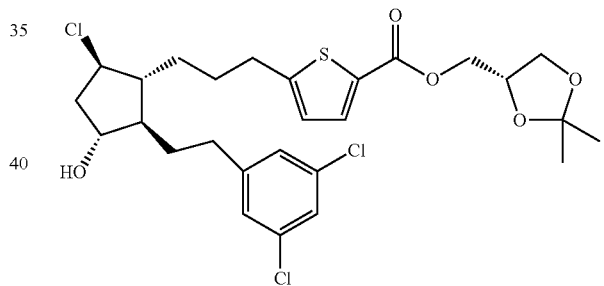

(R)-(−)-2,2-Dimethyl-1,3-dioxolane-4-methanol (572.2 mg, 4.33 mmol) was added to a solution of the carboxylic acid of compound 1 (200 mg, 0.433 mmol), 4-(dimethylamino) pyridine (55.3 mg, 0.453 mmol) and N-(3-dimethylaminopropyl)-N'-ethylcarbodiimide hydrochloride (91.3 mg, 0.476 mmol) in DMF (3.0 mL) at 23° C. After stirring for 16 hours the reaction solution was diluted with EtOAc and washed with 1N HCl, saturated aqueous $NaHCO_3$ then brine. The organic portion was dried ($MgSO_4$), filtered and concentrated in vacuo. Purification of the residue by flash column chromatography (silica gel, 2:1 hex/EtOAc) afforded 211.7 mg (85%) of acetonide protected ester 2 as a clear, viscous oil. The ester 2 (249.0 mg, 0.433 mmol) was stirred at 23° C. in a mixture of 1N HCl:THF (1:1, 3.0 mL) for 24 hours. The reaction mixture was then diluted with EtOAc and washed with water, saturated aqueous $NaHCO_3$ then brine. The organic portion was dried ($MgSO_4$), filtered and concentrated in vacuo. The residue was purified by flash column chromatography (silica gel, 1:1 hex/EtOAc followed by 100% EtOAc) to give 158.8 mg (68%) of the bishydroxy ester compound 3 as a clear, viscous oil.

Scheme 1:

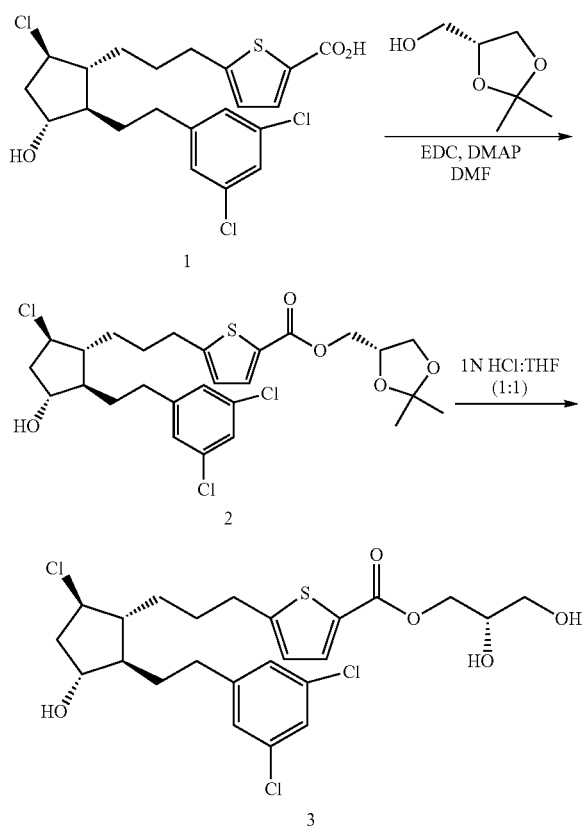

Example 2

Synthesis of ((S)-2,2-dimethyl-1,3-dioxolan-4-yl)
methyl 5-(3-((1R,2R,3R,5R)-5-chloro-2-(3,5-dichlo-
rophenethyl)-3-hydroxycyclopentyl)propyl)
thiophene-2-carboxylate (compound 4)

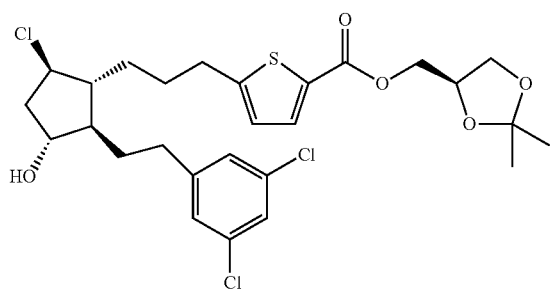 [SMILES: CC1(C)OC[C@H](COC(=O)c2ccc(CCC[C@@H]3[C@@H](CCc4cc(Cl)cc(Cl)c4)[C@H](O)C[C@H]3Cl)s2)O1]

In accordance with the procedures described for the preparation of compound 2 above, use of 100 mg (0.216 mmol) of carboxylic acid of compound 1 and 42.8 mg (0.324 mmol) of (S)-(+)-2,2-dimethyl-1,3-dioxolane-4-methanol afforded 72.3 mg (58%) of acetonide protected ester compound 4.

Example 3

Synthesis of (S)-2,3-dihydroxypropyl 5-(3-((1R,2R, 3R,5R)-5-chloro-2-(3,5-dichlorophenethyl)-3-hy-droxycyclopentyl)propyl)thiophene-2-carboxylate (compound 5)

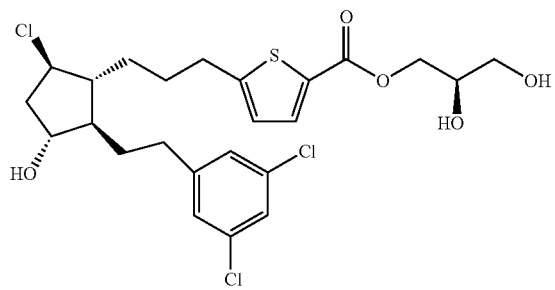 [SMILES: O=C(OC[C@H](O)CO)c1ccc(CCC[C@@H]2[C@@H](CCc3cc(Cl)cc(Cl)c3)[C@H](O)C[C@H]2Cl)s1]

In accordance with the procedures described for the preparation of compound 3 above, use of 72.3 mg (0.125 mmol) of ester 4 provided 43.5 mg (65%) of bishydroxy ester compound 5 as a clear, viscous oil.

Example 4

Synthesis of ((4R,5R)-5-(hydroxymethyl)-2,2-dim-
ethyl-1,3-dioxolan-4-yl)methyl 5-(3-((1R,2R,3R,
5R)-5-chloro-2-(3,5-dichlorophenethyl)-3-hydroxy-
cyclopentyl)propyl)thiophene-2-carboxylate
(compound 6)

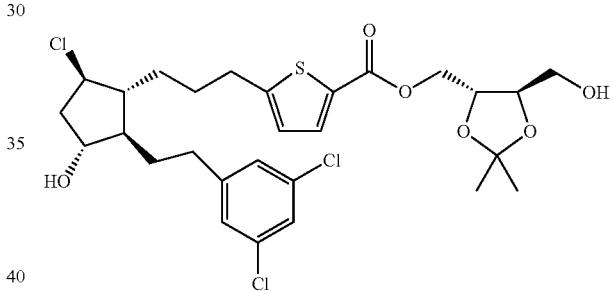

In accordance with the procedures described for the preparation of compound 2 above, use of 100 mg (0.216 mmol) of carboxylic acid 1 and 52.5 mg (0.324 mmol) of (4R,5R)-2,2-dimethyl-1,3-dioxolane-4,5-dimethanol afforded 41.5 mg (31%) of acetonide protected ester compound 6.

Example 5

Synthesis of (2R,3R)-2,3,4-trihydroxybutyl 5-(3-
((1R,2R,3R,5R)-5-chloro-2-(3,5-dichlorophenethyl)-
3-hydroxycyclopentyl)propyl)thiophene-2-carboxy-
late (compound 7)

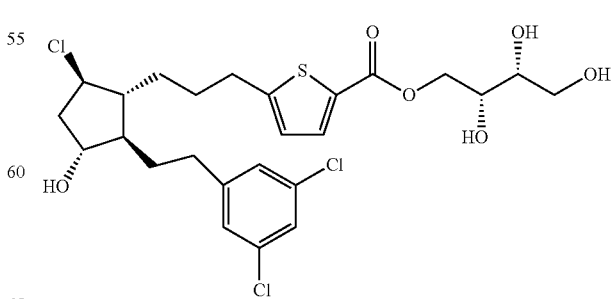

In accordance with the procedures described for the preparation of compound 3 above, use of 41.5 mg (0.069 mmol) of ester 6 provided 27.6 mg (71%) of trishydroxy ester compound 7 as a clear, viscous oil.

Example 6

Synthesis of ((4S,5S)-5-(hydroxymethyl)-2,2-dimethyl-1,3-dioxolan-4-yl)methyl 5-(3-((1R,2R,3R,5R)-5-chloro-2-(3,5-dichlorophenethyl)-3-hydroxycyclopentyl)propyl)thiophene-2-carboxylate (compound 8)

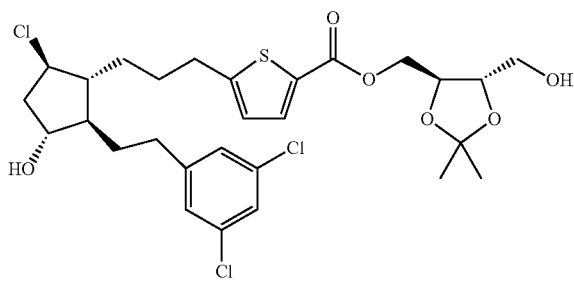 [SMILES: CC1(C)O[C@@H](CO)[C@H](COC(=O)c2ccc(CCC[C@@H]3[C@@H](CCc4cc(Cl)cc(Cl)c4)[C@H](O)C[C@H]3Cl)s2)O1]

In accordance with the procedures described for the preparation of compound 2 above, use of 100 mg (0.216 mmol) of carboxylic acid 1 and 52.5 mg (0.324 mmol) of ((4S,5S)-2,2-dimethyl-1,3-dioxolane-4,5-dimethanol afforded 71.9 mg (55%) of acetonide protected ester compound 8.

Example 7

Synthesis of (2S,3S)-2,3,4-trihydroxybutyl 5-(3-((1R,2R,3R,5R)-5-chloro-2-(3,5-dichlorophenethyl)-3-hydroxycyclopentyl)propyl)thiophene-2-carboxylate (compound 9)

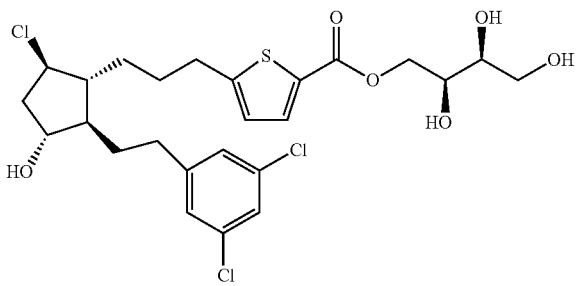 [SMILES: O=C(OC[C@H](O)[C@@H](O)CO)c1ccc(CCC[C@@H]2[C@@H](CCc3cc(Cl)cc(Cl)c3)[C@H](O)C[C@H]2Cl)s1]

In accordance with the procedures described for the preparation of compound 3 above, use of 71.9 mg (0.118 mmol) of ester 8 provided 39.2 mg (59%) of trishydroxy ester compound 9 as a clear, viscous oil.

Example 8

Synthesis of ((4R,4'S,5R)-2,2,2',2'-tetramethyl-[4,4'-bi(1,3-dioxolan)]-5-yl)methyl 5-(3-((1R,2R,3R,5R)-5-chloro-2-(3,5-dichlorophenethyl)-3-hydroxycyclopentyl)propyl)thiophene-2-carboxylate (compound 10)

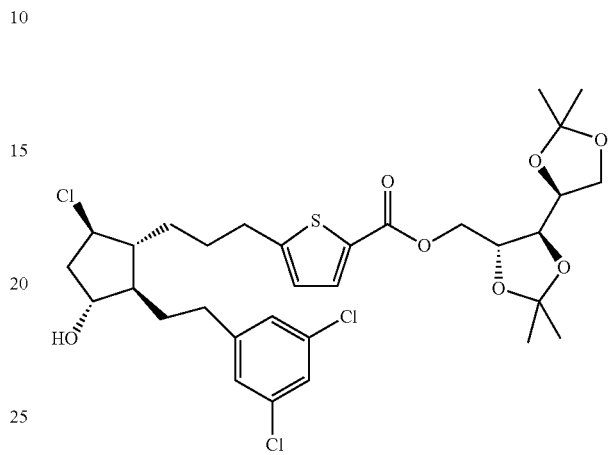

In accordance with the procedures described for the preparation of compound 2 above, use of 100 mg (0.216 mmol) of carboxylic acid 1 and 60.1 mg (0.259 mmol) of ((4S,4'S,5R)-2,2,2',2'-tetramethyl-[4,4'-bi(1,3-dioxolan)]-5-yl)methanol afforded 79.2 mg (52%) of bisacetonide protected ester compound 10.

Example 9

Synthesis of (2R,3R,4S)-2,3,4,5-tetrahydroxypentyl 5-(3-((1R,2R,3R,5R)-5-chloro-2-(3,5-dichlorophenethyl)-3-hydroxycyclopentyl)propyl)thiophene-2-carboxylate (11)

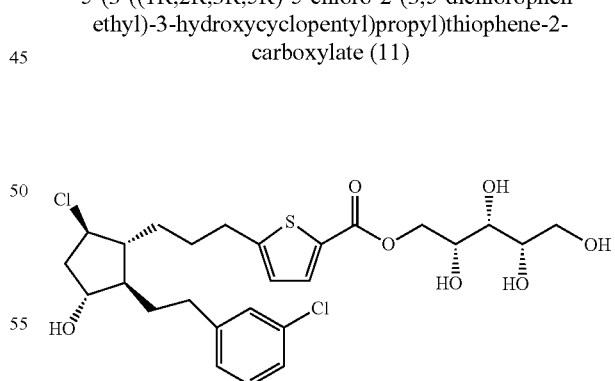

In accordance with the procedures described for the preparation of compound 3 above, use of 79.2 mg (0.117 mmol) of ester 10 provided 11.8 mg (17%) of ester compound 11 as a clear, viscous oil.

Example 10

Synthesis of (S)-2-hydroxy-2-((4R,4'R,5R)-2,2,2',2'-tetramethyl-[4,4'-bi(1,3-dioxolan)]-5-yl)ethyl 5-(3-((1R,2R,3R,5R)-5-chloro-2-(3,5-dichlorophenethyl)-3-hydroxycyclopentyl)propyl)thiophene-2-carboxylate (compound 12)

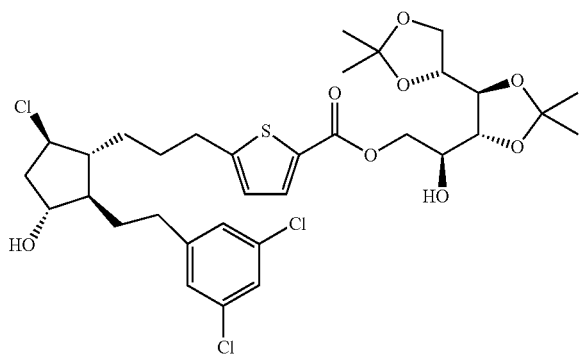

In accordance with the procedures described for the preparation of compound 2 above, use of 100 mg (0.216 mmol) of carboxylic acid 1 and 67.9 mg (0.259 mmol) of (S)-1-((4R,4'R,5R)-2,2,2',2'-tetramethyl-[4,4'-bi(1,3-dioxolan)]-5-yl)ethane-1,2-diol afforded 90.1 mg (59%) of bisacetonide protected ester compound 12.

Example 11

Synthesis of 2,3,4,5,6-pentahydroxyhexyl 5-(3-((1R,2R,3R,5R)-5-chloro-2-(3,5-dichlorophenethyl)-3-hydroxycyclopentyl)propyl)thiophene-2-carboxylate (compound 13)

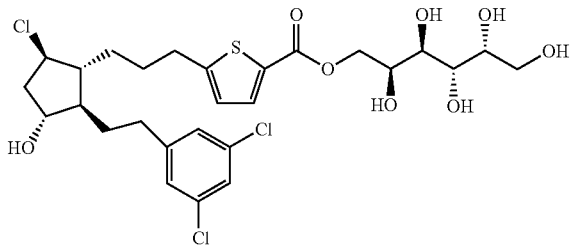 [SMILES: O=C(OC[C@H](O)[C@@H](O)[C@@H](O)[C@H](O)CO)c1ccc(CCC[C@@H]2[C@@H](CCc3cc(Cl)cc(Cl)c3)[C@H](O)C[C@H]2Cl)s1]

In accordance with the procedures described for the preparation of compound 3 above, use of 65.8 mg (0.093 mmol) of ester 12 provided 43.5 mg (75%) of ester 13 as a clear, viscous oil.

Example 12

Synthesis of 3-Hydroxy-2-(hydroxymethyl)propyl 5-(3-((1R,2R,3R,5R)-5-chloro-2-(3,5-dichlorophenethyl)-3-hydroxycyclopentyl)propyl)thiophene-2-carboxylate (compound 14)

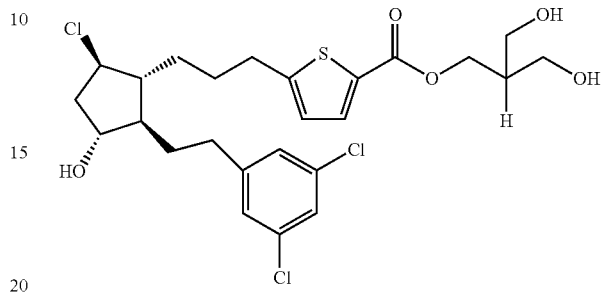

(2,2-Dimethyl-1,3-dioxan-5-yl)methanol (126.6 mg, 0.866 mmol) was added to a solution of the carboxylic acid 1 (200 mg, 0.433 mmol), 4-(dimethylamino)pyridine (55.3 mg, 0.453 mmol) and N-(3-dimethylaminopropyl)-N'-ethylcarbodiimide hydrochloride (91.3 mg, 0.476 mmol) in DMF (3.0 mL) at 23° C. After stirring for 48 h the reaction solution was diluted with EtOAc and washed with 1N HCl, saturated aqueous NaHCO₃ then brine. The organic portion was dried (MgSO₄), filtered and concentrated in vacuo to provide a clear, viscous oil.

The ester obtained above was stirred in a mixture of 1N HCl:THF (1:1, 4 mL) at 23° C. for 16 h. The reaction mixture was diluted with EtOAc and was with water, saturated aqueous NaHCO₃ then brine. The organic portion was dried (MgSO₄), filtered and concentrated in vacuo. Purification of the residue by flash column chromatography (silica gel, 1:1 hex/EtOAc followed by 100% EtOAc) afforded 57.0 mg (24%) of pure dihydroxyester 14 as a clear, colorless oil.

Example 13

Synthesis of 3-Hydroxy-2-(hydroxymethyl)-2-methylpropyl 5-(3-((1R,2R,3R,5R)-5-chloro-2-(3,5-dichlorophenethyl)-3-hydroxycyclopentyl)propyl)thiophene-2-carboxylate (compound 15)

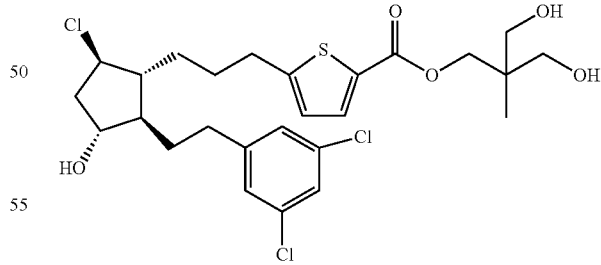

5-Hydroxymethyl-2,2,5-trimethyl-1,3-dioxane (0.26 mL, 1.73 mmol) was added to a solution of the carboxylic acid 1 (200 mg, 0.433 mmol), 4-(dimethylamino)pyridine (55.3 mg, 0.453 mmol) and N-(3-dimethylaminopropyl)-N'-ethylcarbodiimide hydrochloride (91.3 mg, 0.476 mmol) in DMF (3.0 mL) at 23° C. After stirring for 48 h the reaction solution was diluted with EtOAc and washed with 1N HCl, saturated aqueous NaHCO₃ then brine. The organic portion was dried (MgSO₄), filtered and concentrated in vacuo to provide a clear, viscous oil.

The ester obtained above was stirred in a mixture of 1N HCl:THF (1:1, 4 mL) at 23° C. for 16 h. The reaction mixture was diluted with EtOAc and was with water, saturated aqueous NaHCO₃ then brine. The organic portion was dried (MgSO₄), filtered and concentrated in vacuo. Purification of the residue by flash column chromatography (silica gel, 1:1 hex/EtOAc followed by 100% EtOAc) afforded 22.4 mg (9%) of pure dihydroxyester 15 as a clear, colorless oil.

Example 14

Synthesis of (5-(Hydroxymethyl)-1,3-dioxan-5-yl) methyl 5-(3-((1R,2R,3R,5R)-5-chloro-2-(3,5-dichlorophenethyl)-3-hydroxycyclopentyl)propyl) thiophene-2-carboxylate (compound 16)

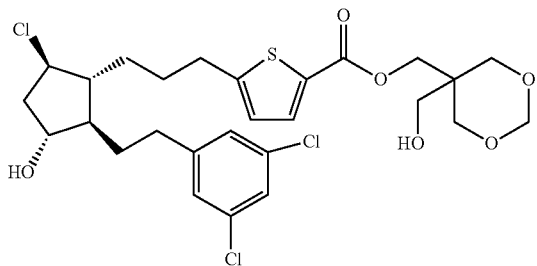 [SMILES: O=C(OCC1(CO)COCOC1)c1ccc(CCC[C@@H]2[C@@H](CCc3cc(Cl)cc(Cl)c3)[C@H](O)C[C@H]2Cl)s1]

(1,3-dioxane-5,5-diyl)dimethanol (256.6 mg, 1.73 mmol) was added to a solution of the carboxylic acid 1 (200 mg, 0.433 mmol), 4-(dimethylamino)pyridine (55.3 mg, 0.453 mmol) and N-(3-dimethylaminopropyl)-N'-ethylcarbodiimide hydrochloride (91.3 mg, 0.476 mmol) in DMF (3.0 mL) at 23° C. After stirring for 48 h the reaction solution was diluted with EtOAc and washed with 1N HCl, saturated aqueous NaHCO₃ then brine. The organic portion was dried (MgSO₄), filtered and concentrated in vacuo Purification of the residue by flash column chromatography (silica gel, 2:1 hex/EtOAc followed by, 1:1 hex/EtOAc) afforded 205.7 mg (80%) of pure hydroxymethylester 16 as a clear, colorless oil.

Example 15

Synthesis of 3-(bis(2-((tetrahydro-2H-pyran-2-yl)oxy)ethyl)amino)-3-oxopropyl 5-(3-((1R,2R,3R,5R)-5-chloro-2-(3,5-dichlorophenethyl)-3-hydroxycyclopentyl)propyl)thiophene-2-carboxylate (compound 17)

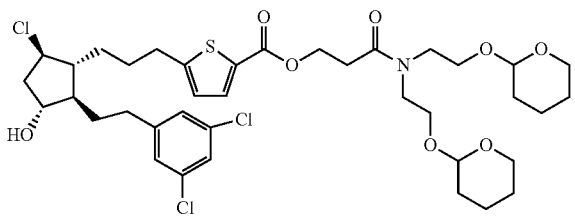 [SMILES: O=C(OCCC(=O)N(CCOC1CCCCO1)CCOC1CCCCO1)c1ccc(CCC[C@@H]2[C@@H](CCc3cc(Cl)cc(Cl)c3)[C@H](O)C[C@H]2Cl)s1]

N-(3-dimethylaminopropyl)-N'-ethylcarbodiimide hydrochloride (91.3 mg, 0.476 mmol) was added to a solution of the carboxylic acid 1 (200 mg, 0.433 mmol), 4-(dimethylamino)pyridine (55.3 mg, 0.453 mmol) and 3-hydroxy-N,N-bis(2-((tetrahydro-2H-pyran-2-yl)oxy)ethyl)propanamide (597.6 mg, 1.73 mmol) in DMF (4.5 mL) at 23° C. After stirring for 48 h the reaction was diluted with EtOAc and washed with 1N HCl, saturated aqueous NaHCO₃ then brine. The organic portion was dried (MgSO₄), filtered and concentrated in vacuo. Flash column chromatography (silica gel, 1:1 hex/EtOAc) afforded 120.4 mg (35%) of pure ester 17 as a clear, colorless oil.

Example 16

Synthesis of 3-(Bis(2-hydroxyethyl)amino)-3-oxopropyl 5-(3-((1R,2R,3R,5R)-5-chloro-2-(3,5-dichlorophenethyl)-3-hydroxycyclopentyl)propyl) thiophene-2-carboxylate (compound 18)

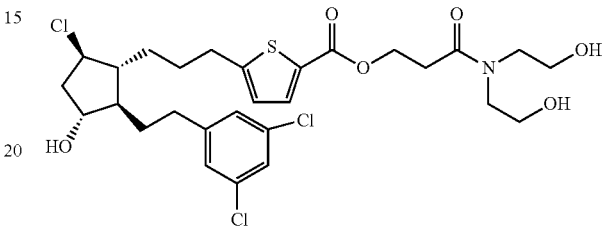

Pyridinium p-toluenesulfonate (38.2 mg, 0.152 mmol) was added to a solution of the ester 17 (120 mg, 0.152 mmol) in MeOH (3.0 mL). The reaction was allowed to stir at 23° C. for 48 h. The solvent was then removed in vacuo. The residue was diluted with EtOAc and washed with 1N HCl, saturated aqueous NaHCO₃ then brine. The organic portion was dried (MgSO₄), filtered and concentrated in vacuo. Purification of the residue by flash column chromatography (silica gel, 100% EtOAc followed by 39:1 EtOAc/MeOH) afforded 54.0 mg (57%) of pure dihydroxyester 18 as a clear, colorless oil.

Example 17

Synthesis of 3-((1,3-bis((tetrahydro-2H-pyran-2-yl)oxy)propan-2-yl)amino)-3-oxopropyl 5-(3-((1R,2R,3R,5R)-5-chloro-2-(3,5-dichlorophenethyl)-3-hydroxycyclopentyl)-propyl)thiophene-2-carboxylate (compound 19)

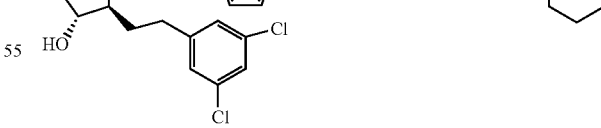

N-(3-dimethylaminopropyl)-N'-ethylcarbodiimide hydrochloride (91.3 mg, 0.476 mmol) was added to a solution of the carboxylic acid 1 (200 mg, 0.433 mmol), 4-(dimethylamino) pyridine (55.3 mg, 0.453 mmol) and N-(1,3-bis((tetrahydro-2H-pyran-2-yl)oxy)propan-2-yl)-3-hydroxypropanamide (574 mg, 1.73 mmol) in DMF (4.5 mL) at 23° C. After stirring for 48 h the reaction was diluted with EtOAc and washed with 1N HCl, saturated aqueous NaHCO₃ then brine. The organic portion was dried (MgSO₄), filtered and concentrated in vacuo. Flash column chromatography (silica gel, 1:1 hex/EtOAc) afforded 60.7 mg (18%) of pure ester 19 as a clear, colorless oil.

Example 18

Synthesis of 3-((1,3-Dihydroxypropan-2-yl)amino)-3-oxopropyl 5-(3-((1R,2R,3R,5R)-5-chloro-2-(3,5-dichlorophenethyl)-3-hydroxycyclopentyl)propyl)thiophene-2-carboxylate (compound 20)

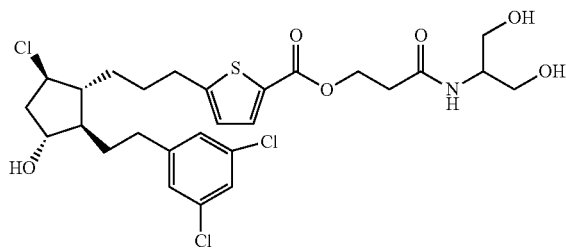 [SMILES: O=C(CCOC(=O)c1ccc(CCC[C@@H]2[C@@H](CCc3cc(Cl)cc(Cl)c3)[C@H](O)C[C@H]2Cl)s1)NC(CO)CO]

Pyridinium p-toluenesulfonate (19.6 mg, 0.078 mmol) was added to a solution of the ester 19 (60.7 mg, 0.078 mmol) in MeOH (3.0 mL). The reaction was allowed to stir at 23° C. for 48 h. The solvent was then removed in vacuo. The residue was diluted with EtOAc and washed with 1N HCl, saturated aqueous NaHCO$_3$ then brine. The organic portion was dried (MgSO$_4$), filtered and concentrated in vacuo. Purification of the residue by flash column chromatography (silica gel, 100% EtOAc followed by 19:1 EtOAc/MeOH) afforded 37.2 mg (79%) of pure dihydroxyester 20 as a clear, colorless oil.

What is claimed is:

1. A compound having the formula:

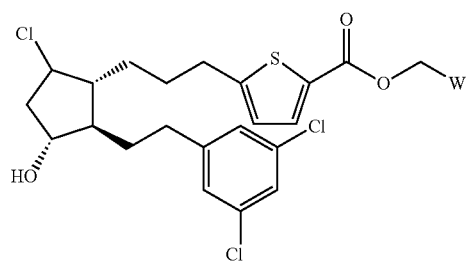

wherein;

W is selected from the group consisting of:

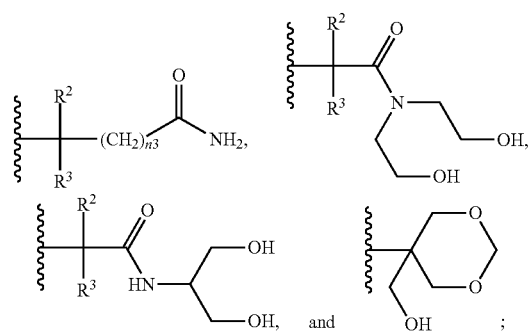

$R^2$ is independently selected from the group consisting of H, $C_1$-$C_6$ alkyl, $C_1$-$C_6$ hydroxyalkyl, and —OH;

$R^3$ is independently H, $C_1$-$C_6$ alkyl, $C_1$-$C_6$ hydroxyalkyl, or —OH; and n3 is 0-3.

2. The compound of claim 1 wherein $R^2$ is —OH and $R^3$ is H or CH$_3$.

3. The compound of claim 1 wherein $R^2$ and $R^3$ are H.

4. The compound of claim 1 wherein $R^2$ and $R^3$ are CH$_2$OH.

5. The compound of claim 1 selected from the group consisting of:

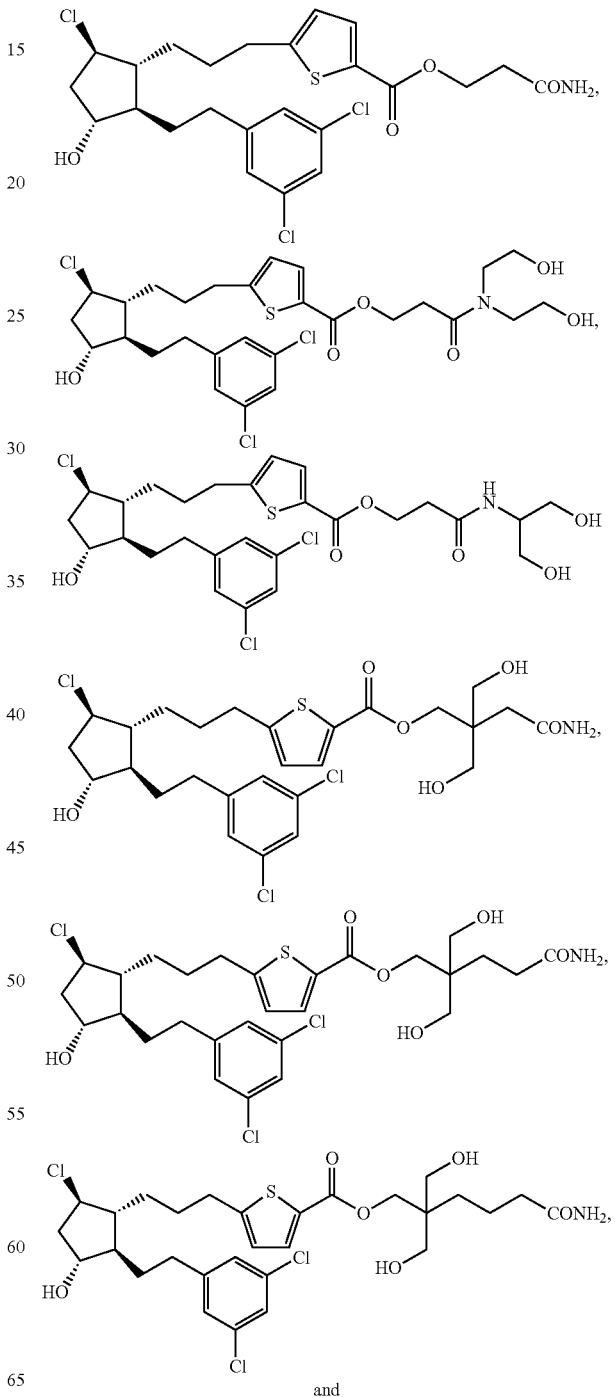

and

45
-continued
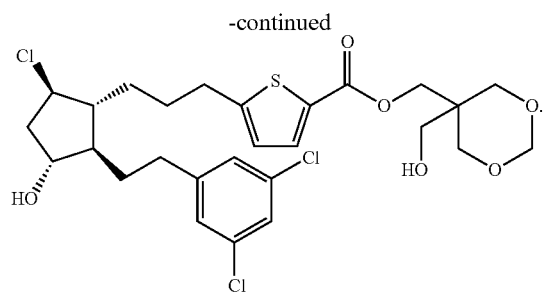
6. A compound selected from the group consisting of:
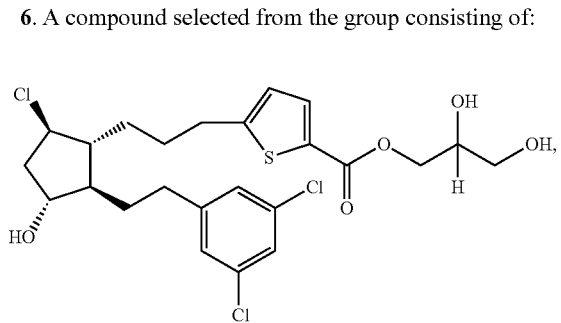
46
-continued
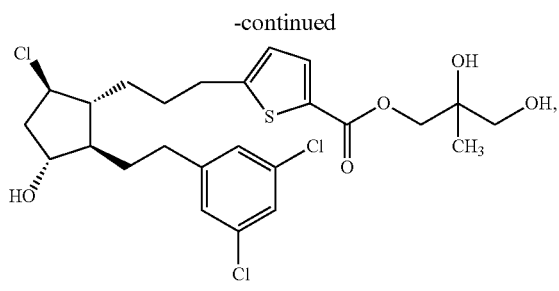
and
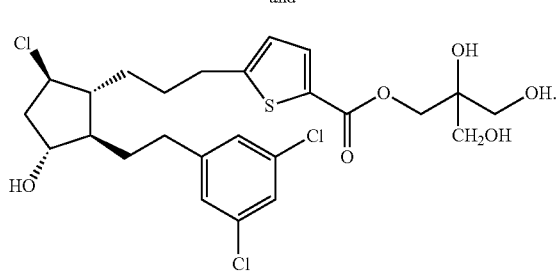
* * * * *

UNITED STATES PATENT AND TRADEMARK OFFICE
CERTIFICATE OF CORRECTION

PATENT NO. : 9,090,595 B2  
APPLICATION NO. : 14/185556  
DATED : July 28, 2015  
INVENTOR(S) : Robert M. Burk et al.

Page 1 of 4

It is certified that error appears in the above-identified patent and that said Letters Patent is hereby corrected as shown below:

Specification

In column 1, line 53, delete "Optipranalol®" and insert -- Optipranolol® --, therefor.

In column 2, line 36, delete "interaylene," and insert -- interarylene, --, therefor.

In column 3, line 66, delete ""alkenylene," and insert -- "alkenylene", --, therefor.

In column 4, line 12-13, delete "(Original) The" and insert -- The --, therefor.

In column 9, line 61, delete "(Original) The" and insert -- The --, therefor.

In column 10, line 58, delete "interaylene," and insert -- interarylene, --, therefor.

In column 11, line 44-45, delete "hydroxy alkyl" and insert -- hydroxyalkyl --, therefor.

In column 13, line 67, delete "hydroxy alkyl," and insert -- hydroxyalkyl, --, therefor.

In column 15, line 30, delete "R4" and insert -- $R^4$ --, therefor.

In column 15, line 30, delete "C1-C6" and insert -- $C_1$-$C_6$ --, therefor.

In column 15, line 31, delete "C1-C6" and insert -- $C_1$-$C_6$ --, therefor.

In column 15, line 42, delete "by 4" and insert -- by --, therefor.

In column 15, line 43, delete "The" and insert -- 42. The --, therefor.

In column 15, in Structure, line 50-54, delete " 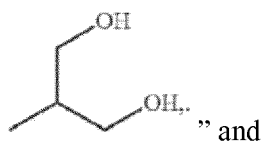 " and insert -- 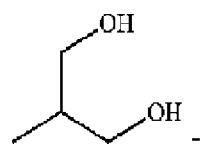 --, therefor.

Signed and Sealed this  
Nineteenth Day of January, 2016

Michelle K. Lee  
*Director of the United States Patent and Trademark Office*

In column 15, in Structure, line 10-18, delete
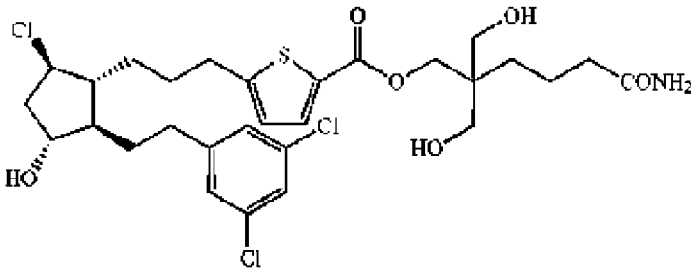
" " and insert
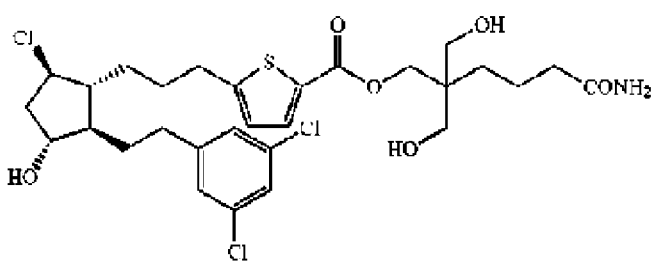
-- . --, therefor.
In column 17, line 36, delete "hydroxy alkyl," and insert -- hydroxyalkyl, --, therefor.
In column 19, in Structure, line 35-44, delete
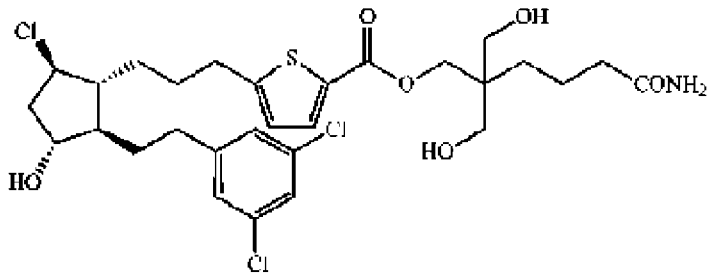
" " and insert
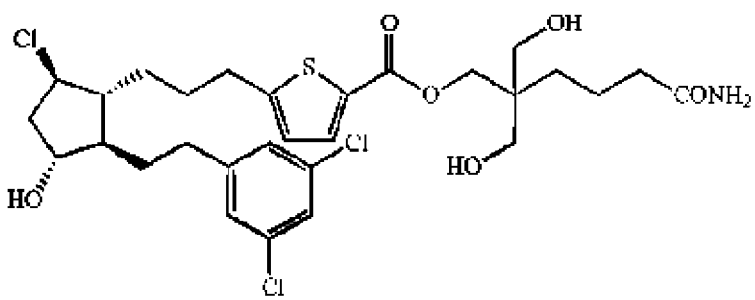
-- . --, therefor.
In column 27-28, in Structure, line 1-17, delete "
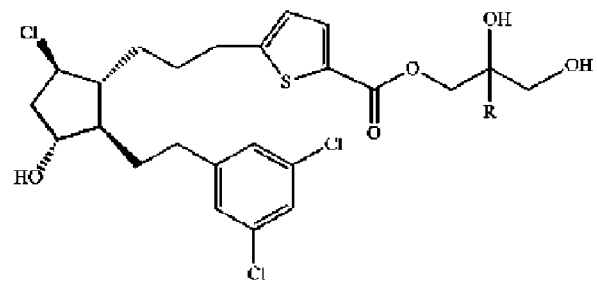
"

CERTIFICATE OF CORRECTION (continued)
U.S. Pat. No. 9,090,595 B2 and insert -- 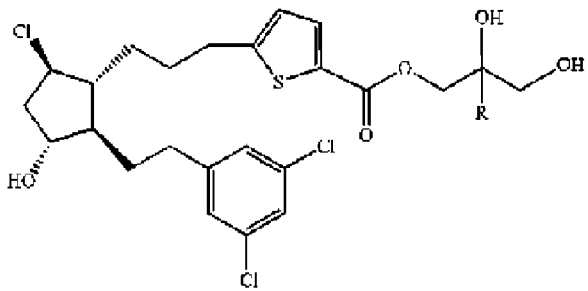 . --, therefor.

In column 27-28, in Structure, line 24-34, delete

" 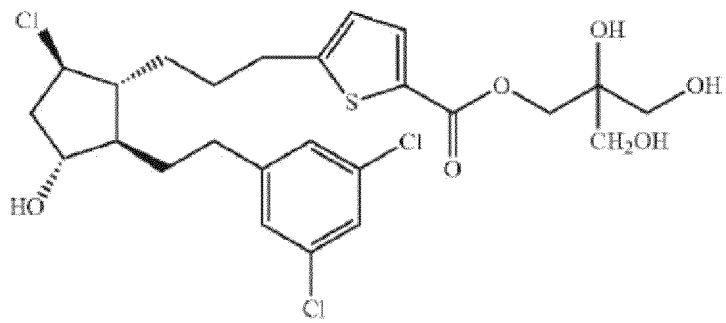 " and insert

-- 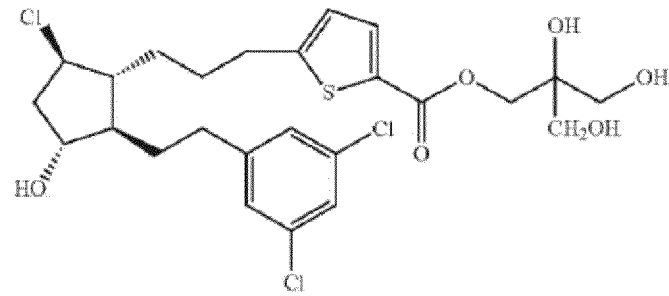 . --, therefor.

In column 30, line 48, delete "XIII XIV." and insert -- XIII, XIV. --, therefor.

In column 33, line 38, delete "chloprostenol," and insert -- cloprostenol, --, therefor.

In column 33, line 39, delete "chloprostenol," and insert -- cloprostenol, --, therefor.

In column 34, line 28, delete "(R)" and insert -- ((R) --, therefor.

In column 34, line 31, delete "2" and insert -- 2) --, therefor.

In column 36, line 45, delete "(31'%)" and insert -- (31%) --, therefor.

Claims

In column 43, line 49, in claim 1, delete "wherein;" and insert -- wherein: --, therefor.

In column 44, line 1, in claim 1, delete "$C_1$-$C_6$hydroxyalkyl," and insert -- $C_1$-$C_6$ hydroxyalkyl, --, therefor.

CERTIFICATE OF CORRECTION (continued)
U.S. Pat. No. 9,090,595 B2

In column 44, in Structure, line 30-37, in claim 5, delete

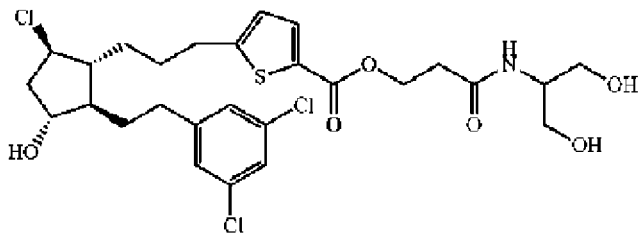

" and insert

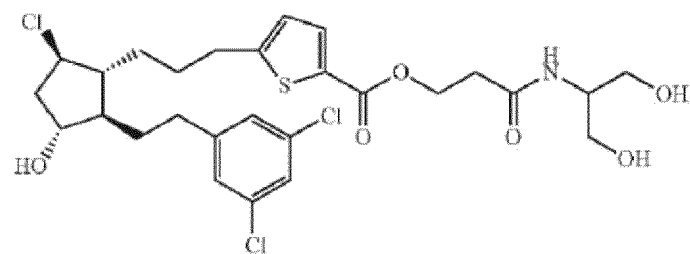

--, therefor.